United States Patent
Weiler et al.

(10) Patent No.: US 10,842,680 B1
(45) Date of Patent: Nov. 24, 2020

(54) METHODS AND SYSTEMS FOR FITTING COMPRESSION GARMENTS FROM DIGITAL IMAGERY

(71) Applicants: Michael J. Weiler, Atlanta, GA (US); Nathan Daniel Frank, Atlanta, GA (US)

(72) Inventors: Michael J. Weiler, Atlanta, GA (US); Nathan Daniel Frank, Atlanta, GA (US)

(*) Notice: Subject to any disclaimer, the term of this patent is extended or adjusted under 35 U.S.C. 154(b) by 0 days.

(21) Appl. No.: 16/558,074

(22) Filed: Aug. 31, 2019

(51) Int. Cl.
| | |
|---|---|
| G06K 9/00 | (2006.01) |
| A61F 13/08 | (2006.01) |
| A61F 13/00 | (2006.01) |
| A41H 1/00 | (2006.01) |
| G16H 20/00 | (2018.01) |
| G06T 7/62 | (2017.01) |
| A61B 5/107 | (2006.01) |

(52) U.S. Cl.
CPC .......... *A61F 13/08* (2013.01); *A41H 1/00* (2013.01); *A61B 5/1079* (2013.01); *A61F 13/00987* (2013.01); *G06T 7/62* (2017.01); *G16H 20/00* (2018.01); *G06T 2207/10028* (2013.01); *G06T 2207/30196* (2013.01)

(58) Field of Classification Search
None
See application file for complete search history.

(56) References Cited

U.S. PATENT DOCUMENTS

| | | |
|---|---|---|
| 4,406,544 A | 9/1983 | Takada et al. |
| 4,885,844 A | 12/1989 | Chun |
| 5,107,837 A * | 4/1992 | Ophir ................. A61B 5/441 600/437 |
| 5,450,750 A | 9/1995 | Abler |
| 5,530,652 A | 6/1996 | Croyle et al. |
| 6,415,199 B1 | 7/2002 | Liebermann |

(Continued)

FOREIGN PATENT DOCUMENTS

| | | |
|---|---|---|
| EP | 1756343 A1 | 2/2007 |
| EP | 1882447 A1 | 1/2008 |

(Continued)

OTHER PUBLICATIONS

Stout Gergich et al., "Preoperative assessment enables the early diagnosis and successful treatment of lymphedenna." Cancer: Interdisciplinary International Journal of the American Cancer Society 112, No. 12 (2008): 2809-2819. (Year: 2008).*

(Continued)

*Primary Examiner* — Feng Niu
(74) *Attorney, Agent, or Firm* — Thomas Horstemeyer, LLP

(57) ABSTRACT

The present disclosure includes methods and systems to generate compression garment fit information from 3D images taken of one or more body parts of a patient indicated for application of compression therapy. The body parts can include legs or arms or other areas. Three-dimensional ("3D") imaging information can be used to derive compression garment fit information, where the shape description information includes for each body part: tissue compressibility information, outer circumference information, and length information. Comparisons between corresponding body parts on a person can also be conducted.

19 Claims, 8 Drawing Sheets

(56) References Cited

U.S. PATENT DOCUMENTS

| | | | |
|---|---|---|---|
| 6,463,351 B1 | 10/2002 | Clynch | |
| 6,546,309 B1 | 4/2003 | Gazzuolo | |
| 6,888,640 B2 | 5/2005 | Spina et al. | |
| 6,927,858 B2 | 8/2005 | Boone et al. | |
| 7,039,486 B2 | 5/2006 | Wang | |
| 7,043,329 B2 | 5/2006 | Dias et al. | |
| 7,092,782 B2 | 8/2006 | Lee | |
| 7,398,133 B2 | 7/2008 | Wannier et al. | |
| 7,421,306 B2 | 9/2008 | Adiseshan | |
| 7,594,896 B2 | 9/2009 | Sakai et al. | |
| 7,615,018 B2 | 11/2009 | Nelson et al. | |
| 8,320,648 B2* | 11/2012 | Mailling | B33Y 80/00 382/128 |
| 8,387,266 B2 | 3/2013 | Eddy | |
| 8,491,514 B2* | 7/2013 | Creighton | A61F 13/10 602/60 |
| 8,813,378 B2 | 8/2014 | Grove | |
| 9,161,736 B2* | 10/2015 | Waki | A61B 8/4461 |
| 9,161,878 B1* | 10/2015 | Pamplin | A61H 7/001 |
| 9,271,890 B1* | 3/2016 | Pamplin | A61H 23/02 |
| 9,345,271 B2 | 5/2016 | Collins et al. | |
| 9,777,413 B2* | 10/2017 | Messier | D04B 9/52 |
| 10,028,727 B2* | 7/2018 | Inoue | A61B 8/469 |
| 10,045,581 B2* | 8/2018 | Weiler | G16H 20/30 |
| 10,232,165 B2* | 3/2019 | Hyde | A61H 9/0078 |
| 10,251,438 B2* | 4/2019 | Weiler | A41H 3/04 |
| 10,285,902 B2* | 5/2019 | Pamplin | A61H 7/001 |
| 10,390,571 B2* | 8/2019 | McKeen | A41C 3/0057 |
| 10,413,253 B2* | 9/2019 | Oh | G16H 30/40 |
| 10,455,868 B2* | 10/2019 | Duffy | A41D 1/04 |
| 10,492,544 B2* | 12/2019 | McKeen | A41C 3/06 |
| 2002/0004763 A1 | 1/2002 | Lam | |
| 2002/0138170 A1 | 9/2002 | Onyshkevych et al. | |
| 2002/0178061 A1 | 11/2002 | Lam | |
| 2002/0188372 A1 | 12/2002 | Lane et al. | |
| 2005/0154487 A1 | 7/2005 | Wang | |
| 2006/0287877 A1 | 12/2006 | Wannier et al. | |
| 2007/0005174 A1 | 1/2007 | Thomas | |
| 2007/0060816 A1* | 3/2007 | Simpkin | A61B 5/1077 600/430 |
| 2007/0073144 A1* | 3/2007 | Simpkin | A61B 5/1077 600/430 |
| 2007/0293752 A1* | 12/2007 | Simpkin | G01S 13/86 600/407 |
| 2008/0255920 A1 | 10/2008 | Vandergriff et al. | |
| 2008/0262344 A1* | 10/2008 | Brummett | A61B 5/0275 600/426 |
| 2009/0099457 A1 | 4/2009 | Barnes | |
| 2009/0232378 A1* | 9/2009 | Nakamura | G06T 7/337 382/131 |
| 2009/0234489 A1 | 9/2009 | Healy | |
| 2009/0316965 A1 | 12/2009 | Mailling | |
| 2010/0023421 A1 | 1/2010 | Wannier et al. | |
| 2010/0056973 A1* | 3/2010 | Farrow | A61F 13/08 602/63 |
| 2010/0069744 A1* | 3/2010 | Simpkin | G01S 13/90 600/425 |
| 2010/0312143 A1 | 12/2010 | Kim | |
| 2012/0041344 A1 | 2/2012 | Flodmark | |
| 2014/0052028 A1 | 2/2014 | Wright et al. | |
| 2014/0056499 A1* | 2/2014 | Park | G06T 5/003 382/131 |
| 2014/0200494 A1 | 7/2014 | Winkler | |
| 2014/0259267 A1 | 9/2014 | Nordstrom | |
| 2014/0277663 A1 | 9/2014 | Gupta et al. | |
| 2014/0300907 A1 | 10/2014 | Kimmel | |
| 2015/0051524 A1 | 2/2015 | Messier | |
| 2015/0081472 A1 | 3/2015 | Levin et al. | |
| 2015/0216477 A1 | 8/2015 | Sayegh et al. | |
| 2015/0302594 A1 | 10/2015 | Moore et al. | |
| 2016/0120734 A1 | 5/2016 | Ishikawa et al. | |
| 2016/0235354 A1 | 8/2016 | Weiler et al. | |
| 2017/0120080 A1* | 5/2017 | Phillips | A61N 7/022 |
| 2018/0168261 A1* | 6/2018 | Weiler | A41H 3/04 |
| 2018/0303179 A1* | 10/2018 | Konukoglu | A61F 13/08 |
| 2019/0205441 A1* | 7/2019 | Shelton, IV | G16H 20/40 |
| 2019/0208850 A1* | 7/2019 | Weiler | A41H 3/007 |
| 2020/0000165 A1* | 1/2020 | Wang | A41H 1/02 |
| 2020/0000676 A1* | 1/2020 | Pamplin | A61H 7/001 |

FOREIGN PATENT DOCUMENTS

| | | | | |
|---|---|---|---|---|
| WO | WO-2005106087 A1 * | 11/2005 | | D04B 15/56 |
| WO | 2007085864 A2 | 8/2007 | | |
| WO | 2014037939 A1 | 3/2014 | | |
| WO | 2015120271 A1 | 8/2015 | | |
| WO | 2015155331 A1 | 10/2015 | | |
| WO | WO-2019157486 A1 * | 8/2019 | | A61B 5/0082 |

OTHER PUBLICATIONS

Johnson, Kristine C., Amanda G. Kennedy, and Sharon M. Henry. "Clinical measurements of lymphedema." Lymphatic research and biology 12.4 (2014): 216-221.

Garza, Ramon, et al. "A comprehensive overview on the surgical management of secondary lymphedema of the upper and lower extremities related to prior oncologic therapies." BMC cancer 17.1 (2017): 468.

Hidding, Janine T., et al. "Measurement properties of instruments for measuring of lymphedema: systematic review." Physical therapy 96.12 (2016): 1965-1981.

Armer, Jane M. "The problem of post-breast cancer lymphedema: impact and measurement issues." Cancer investigation 23.1 (2005): 76-83.

Tan, Chee-Wee, Fiona Coutts, and Cathy Bulley. "Measurement of lower limb volume: agreement between the vertically oriented perometer and a tape measure method." Physiotherapy 99.3 (2013): 247-251.

Ridner, Sheila H., et al. "Comparison of upper limb volume measurement techniques and arm symptoms between healthy volunteers and individuals with known lymphedema." Lymphology 40.1 (2007): 35-46.

Yahathugoda, Channa, et al. "Use of a novel portable three-dimensional imaging system to measure limb volume and circumference in patients with filarial lymphedema." The American journal of tropical medicine and hygiene 97.6 (2017): 1836-1842.

Chromy, Adam, et al. "Limb volume measurements: comparison of accuracy and decisive parameters of the most used present methods." Springerplus 4.1 (2015): 707.

Faisal, Siddique Hafiz, et al. "Effect of elastane linear density on compression pressure of V-shaped compression socks." Industria Textila 69.2 (2018): 118-127.

Partsch, Hugo, Bernhard Partsch, and Walter Braun. "Interface pressure and stiffness of ready made compression stockings: comparison of in vivo and in vitro measurements." Journal of Vascular Surgery 44.4 (2006): 809-814.

Hill, Jessica A., et al. "The variation in pressures exerted by commercially available compression garments." Sports Engineering 18.2 (2015): 115-121.

Rogan, Slavko, et al. "Therapy modalities to reduce lymphoedema in female breast cancer patients: a systematic review and meta-analysis." Breast cancer research and treatment 159.1 (2016): 1-14.

Tanaka, Nobuyuki, et al. "Scale-independent stiffness measurement of upper limbs with lymphedema by a circular compression." 2012 Annual International Conference of the IEEE Engineering in Medicine and Biology Society. IEEE, 2012.

Armer, Jane M., et al. "Best-practice guidelines in assessment, risk reduction, management, and surveillance for post-breast cancer lymphedema." Current breast cancer reports 5.2 (2013): 134-144.

Moein, Hadi, et al. "Evaluating the efficacy of an active compression brace on orthostatic cardiovascular responses." PloS one 12.11 (2017): e0187885.

Fuller, N. J., et al. "Predicting composition of leg sections with anthropometry and bioelectrical impedance analysis, using magnetic resonance imaging as reference." Clinical Science 96.6 (1999): 647-657.

(56) References Cited

OTHER PUBLICATIONS

Troynikov, O., et al. "Factors influencing the effectiveness of compression garments used in sports." Procedia Engineering2.2 (2010): 2823-2829.

Kayiran, Oguz & De La Cruz, Carolyn & Tane, Kaori & Soran, Atilla. (2017). Lymphedema: From diagnosis to treatment. Turkish Journal of Surgery. 33. 51-57. 10.5152/turkjsurg.2017.3870.

Tidhar, Dorit, et al. "Measurement issues in anthropometric measures of limb volume change in persons at risk for and living with lymphedema: a reliability study." Journal of personalized medicine 5.4 (2015): 341-353.

Leung, W. Y., et al. "Pressure prediction model for compression garment design." Journal of Burn Care & Research 31.5 (2010): 716-727.

Jung, Minji, et al. "Reference values of bioelectrical impedance analysis for detecting breast cancer-related lymphedema." Medicine 97.44 (2018).

Zhao, Lihuan, et al. "Compression sleeves design based on Laplace Laws." Journal of Textile Engineering & Fashion Technology 2.2 (2017): 314-320.

Wang, Lijing, Martin Felder, and Jackie Y. Cai. "Study of properties of medical compression garment fabrics." Journal of Fiber Bioengineering and Informatics 4.1 (2011): 15-22.

Salleh, Mohamed Najib, et al. "Development of a flexible customized compression garment design system." The 2012 International Conference on Advanced Mechatronic Systems. IEEE, 2012.

Perrey, Stephane. "Compression garments: Evidence for their physiological effects (P208)." The Engineering of Sport 7 (2008): 319-28.

Duking, Peter, et al. "Comparison of non-invasive individual monitoring of the training and health of athletes with commercially available wearable technologies." Frontiers in physiology 7 (Mar. 2016).

Venkatraman, Praburaj, and D. J Tyler. "Applications of Compression Sportswear." Materials and Technology for Sportswear and Performance Apparel (Dec. 2015): 171-203.

Belbasis, Aaron, and Franz Konstantin Fuss. "Development of next-generation compression apparel." Procedia Technology 20 (Jan. 2015): 85-90.

Belbasis, Aaron, Franz Konstantin Fuss, and Jesper Sidhu. "Muscle activity analysis with a smart compression Jarmenl." Procedia Engineering 112 (Jan. 2015): 163-168.

Dixon, J. Brandon, and Michael J. Weiler. "Bridging the divide between pathogenesis and detection in lymphedema." Seminars in cell & developmental biology_ vol. 38. Academic Press (Feb. 2015).

Weiler, Michael, and J. Brandon Dixon. "Differential transport function of lymphatic vessels in the rat tail model and the long-term effects of Indocyanine Green as assessed with near-infrared imaging." Frontiers in physiology 4 (Aug. 2013).

The Diagnosis and Treatment of Lymphadema, The NLN Medical Advisory Committee, Updated Feb. 2011 available at http://www.lymphnel.org/pdfDocs/nIntreatmenl.pdf).

Weiler, Michael, Timothy Kassis, and J. Brandon Dixon. "Sensitivity analysis of near-infrared functional lymphatic Imaging." Journal of biomedical optics 17.6 (Jun. 2012): 0660191-06601911.

Nelson, Tyler S., et al. "Minimally invasive method for determining the effective lymphatic pumping pressure in rats using near-infrared imaging." American Journal of Physiology-Regulatory, Integrative and Comparative Physiology 306.5 (Jan. 2014): R281-R290.

Volotao, Carlos FS, et al., "Shape characterization with turning functions," Proceedings of the 17th international Conference on systems, signals and image processing, Editora da Universidade Federal Fluminense. vol. 1, 2010.

R. C. Gonzalez and R. E. Woods, Digital Image Processing, Englewood Cliffs, NJ: Prentice Hall, 2007, Chapter 11 presentation by authors.

International Search Report and Written Opinion for related PCT Application No. PCT/US2017/046325, filed Aug. 10, 2017, dated Oct. 18, 2017.

European Application No. 17840289 Search Report dated Jan. 29, 2019.

Salleh M.N. et al: "Development of a flexible customized compression garment design system", Advanced Mechatronic Systems (ICAMECHS), 2012 International Conference on, IEEE, (2012) pp. 175-179.

European Application No. 19155337.9 Search Report dated Jul. 6, 2019.

D'apuzzo: "Human Body Measurement Newsletter—You Press the Button—we do the rest", Aug. 1, 2009 (Aug. 1, 2009), pp. 1-7, XP55159934, Retrieved from the Internet: URL:http://www.hometrica.ch/docs/newsletter0901. pdf [retrieved on Jan. 5, 2015] p. 4.

\* cited by examiner

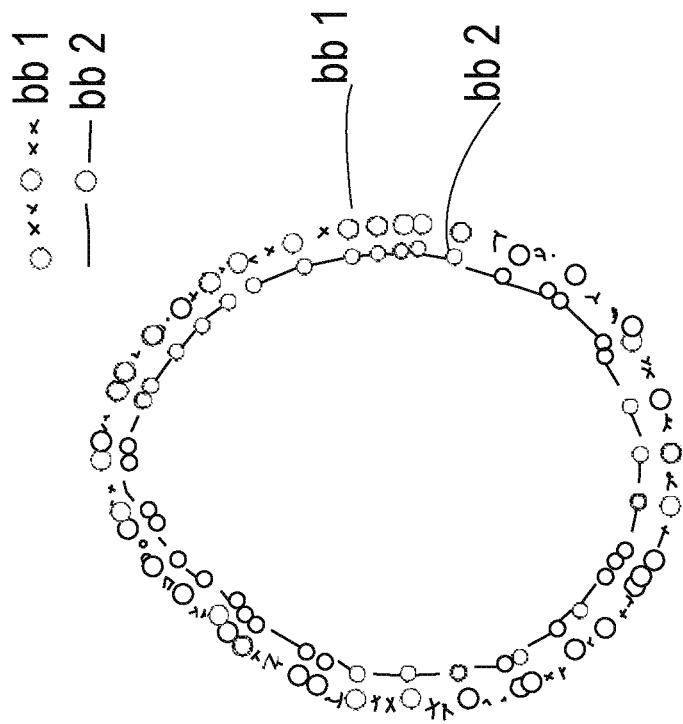
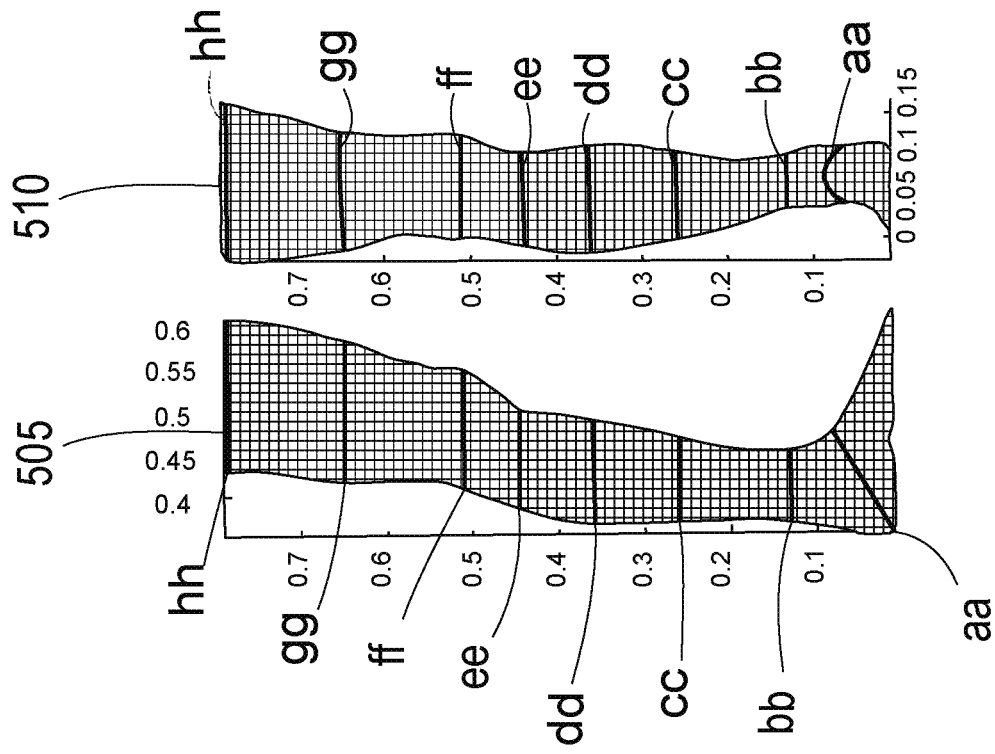
FIG. 4A
FIG. 4B

METHODS AND SYSTEMS FOR FITTING COMPRESSION GARMENTS FROM DIGITAL IMAGERY

FIELD OF THE DISCLOSURE

The present disclosure comprises methods and systems to generate compression garment fit information from 3D images taken of one or more body parts of a patient indicated for application of compression therapy. The body parts can comprise legs or arms or other areas. Three-dimensional ("3D") imaging information can be used to derive compression garment fit information, where the shape description information can include for each body part: tissue compressibility information, outer circumference information, and length information. Comparisons between corresponding body parts on a person can also be conducted.

BACKGROUND OF THE DISCLOSURE

"Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as hypotonic fluid overload, which allows the movement of water into the intracellular space, or hypoproteinemia, which decreases the concentration of plasma proteins and permits the passage of fluid out of the blood vessels in to the tissue spaces. Other factors can include poor lymphatic drainage (known as "lymphedema"), conditions associated with an increased capillary pressure (e.g., excessive retention of salt and/or water), heart failure, and conditions associated with increased capillary pressure, such as inflammation.

When a person is symptomatic of edema, early diagnosis and treatment is imperative. As swelling increases, more pressure is exerted on surrounding cells, tissues and blood vessels. As these areas are squeezed from the increase of fluid and from the natural body response to increased inflammation (as a component of "first response" to an injury), more tissues die, more fluids are released, and the amount of edema presented increases. As edema increases, there is more potential for this "cascade effect" to continue, to result in even more damage. Thus, early diagnosis and regular patient monitoring can be critical to identify swelling occurring prior to the generation of the "edema cascade."

Compression garments can be used to prevent and or treat edema and a number of conditions that cause swelling in patient body parts or body areas. In this regard, edema, which as indicated, presents as excessive interstitial fluid accumulation, may arise from a variety of illnesses and conditions, including venous valvular insufficiency, post-phlebotic syndrome, post-traumatic swelling, postoperative swelling, congestive heart failure-related swelling, hypoalbuminemia-related swelling, drug induced swelling, and lymphedema. When properly fitted and worn by a patient with compliance, compression garments can reverse venous hypertension, augment skeletal muscle pump, facilitate venous return and improve lymphatic drainage. Accordingly, compression garments can be used in patients symptomatic of edema, lymphedema, CVI, pregnancy, and venous ulcers. Compression garments can also be used prophylactically to prevent DVT.

In the treatment of edema-like conditions, compression garments can address patient body part or body area swelling by increasing transport and reducing stagnation of interstitial fluids. Such interstitial fluids operate to increase nutrient delivery to tissue, remove waste from tissues, reduce pain from swelling, and decrease the risk of infection.

In addition to therapeutic effectiveness, compression garments are an increasingly popular clothing item worn by athletes and active individuals with the goal of enhancing recovery from exercise. While the actual mechanism of action for compression clothing remains largely unknown today, it is generally hypothesized that when compression garments are used during recovery, muscle swelling is reduced. Improvements in recovery after exercise are seen by both men and women, who can be well-trained athletes or "weekend warriors." Generally, it seems likely that compression garments display greater overall benefits following higher amounts of, or greater intensities of, exercise. Notwithstanding the lack of clear knowledge about how compression garments assist in athletic recovery, it is nonetheless important to provide persons in need of treatment with compression garments that fit well.

For both therapeutic and post-exercise use, proper fitting of compression garments is important if only because ill-fitting garments will not provide the intended/prescribed amount of compression therapy to the person in need of treatment. Existing methods of fitting compression garments for a specific patient are problematic, however. As would be understood, human patient body parts or body areas that may be fitted with compression garments are not regularly shaped, and some may be quite complex in surface shape or morphology, such as in patients with advanced lymphedema or those who are morbidly obese, for example.

A further concern in the design of a compression garment is patient comfort. A compression garment may provide proper compression characteristics, but if the wearer experiences discomfort due to pinching, chaffing, buckling, or other reasons, she is unlikely to be compliant in wearing the compression garment and, thus, may not achieve therapeutic benefits. For example, the noncompliance rate for graduated compression stockings has been reported to be 30%-65%. Commonly cited reasons include, among other things, pain, discomfort, difficulty donning the stockings, perceived ineffectiveness, excessive heat, and skin irritation. Of course, if a patient fails to wear a compression garment that is prescribed for a potentially chronic or already chronic condition, that condition can become worse and, perhaps, irreversible damage could result. Thus, improved patient compression garment compliance is a need today.

The compression garment must be able to apply the intended/prescribed compression levels and compression levels for each area of an affected patient body part. The proper compression must be applied in the proper direction (or "vectors"). In other words, in use, a compression garment must have the properties of both good fit and appropriately applied therapeutic compression values to effectively provide the intended/prescribed level of compression therapy to a person in need thereof, as well as to prevent harm from occurring to the patient caused by a poorly fitting and/or incorrectly generated compression garment.

Traditionally, compression garment fit information has been generated primarily by use of a tape measure to obtain physical measurements for a person in need of fitting. When sizing and fitting certain medical compression garments, especially custom made-to-measure garments, two sets of circumference measurements are taken with the tape measure: outer skin circumference and tensioned skin circumference. Outer skin circumference is acquired without any compression on the skin—it is the circumference of the surface of the measured body part. Tensioned skin circumference is taken by pulling the tape measure tight to compress the skin at the same body part location where a corresponding outer skin circumference measurement was taken. To measure outer skin circumference, the tape measure is laid flat on the skin, whereas it is pulled tight to constrict into the skin when taking a tension circumference measurement. The difference between the outer skin circumference and the tensioned skin circumference is dictated by tissue composition, which changes based upon body region and disease stage (among other less impactful factors).

As would be appreciated, tensioned skin circumference measurements are always smaller than outer skin circumference measurements, and the difference is more marked when the patient body part is more compressible. Conversely, the difference is less marked when the body part location comprises less compressible tissue, such as in a bony area or with fibrotic tissue. The tensioned skin circumference gives an indication of the size of the limb under compression as applied by a compression garment when worn by the patient.

Between patients, there can be marked differences between the outer skin circumference and the tensioned skin circumference at the same body part location. Moreover, within a single patient, there can be marked differences between outer skin circumference and the tensioned skin circumference of different body part locations for the patient. Such differences can often be attributed to medical indications, such as edema or lymphedema, or to a presence of adipose and/or fibrotic tissue at the locations where the respective circumference measurements are generated.

For example, a subject with extensive adipose tissue would have a larger difference between the measured body part circumference under tension and the outer skin circumference for the same location than a person of healthy weight because in the former the tissue is more compressible. Conversely, a subject with extensive fibrosis would have a smaller difference between outer skin circumference and tensioned skin circumference because the tissue is firmer and less compressible when fibrosis is present. It would also be appreciated that bony regions such as the ankle and wrist areas will have a smaller difference between outer skin circumference and tensioned skin circumference than an upper thigh and upper arm because these bony regions would be less compressible than fleshy regions.

The differences in body part outer skin circumference and tensioned skin circumferences when generating compression garment fit information via tape measurement takes into account the underlying tissue compressibility of the patient's patient body part at each measured location. The combination of both outer skin circumference and tensioned skin circumference can be highly relevant to effective garment fitting at least because the effectiveness of applied compression therapy to the patient depends significantly on the ability of the garment to apply appropriate pressure to generate effects on the patient's lymph and/or venous system. In short, the compression exerted by compression garment will not be transferred to the underlying lymph and/or venous system if the tissue under the skin will absorb or dissipate the applied compression. A garment that is large enough for the patient body part outer skin circumference but that nonetheless is not able to apply an appropriate pressure to the underlying lymph and/or vascular system may then be largely ineffective for the intended treatment use. Conversely, fibrotic tissue may allow "too much" compression to be passed into the underlying lymph and/or venous system because the tissue may be largely incapable of absorbing or dissipating the amount of compression that is expected from "normal" tissue.

As an illustrative example, a first patient and a second patient may have identical outer circumference measurements for the same body part (e.g., leg: leg) and body part area (ankle: ankle). The second patient may nonetheless be symptomatic of lymphedema. When using a tape measurement method, a tensioned skin circumference generated during a measurement event would indicate for the second patient compression garment fit information for a "tighter" compression garment fit than would be indicated by only the outer circumference measurement. The tape measurements will indicate that a compression garment suitable to apply the intended compression level needed to provide a therapeutic amount of compression to the body part of one patient will need to have a smaller compression garment circumference and/or greater compression value incorporated therein—both of which are relevant to the compression garment fit information—than that indicated for the patient who is not symptomatic of lymphedema. For that patient, the compression garment will have to be "tighter" or have an effectively greater amount of tension applied to the body part to generate the same amount of compression therapy to the patient. In other words, each of the two patients will need two different compression garment fit configurations, even though each has the same outer skin circumference for the same body part location. The compression garment fit information generated for each patient will be different in at least these compression-related parameters.

Despite circumference measurements of a body while under tension, and "tensioned circumferences," serving such a critical role in proper compression garment sizing and attendant compression therapy effectiveness, there is wide variability in how tensioned circumferences are measured, even among expertly trained fitters. This creates a lack of standardization and a lack of precision sizing for patient among compression garment fitting and the treatment protocols associated therewith. Nonetheless, tape measurement remains the standard method of generating compression garment fit information today.

Three-dimensional ("3D") imaging is an emerging technique to generate highly accurate geometric measurements of body parts for the fitting of compression garments. The inventors herein have previously disclosed methodologies to generate accurate measurements of patient body part circumferences using the concept of "shape description." As set out in their U.S. Pat. Nos. 10,045,581 and 10,251,438, the disclosures of which are both hereby incorporated by reference in their entireties, such 3D imaging can be used to generate custom-fitted compression garments, as well as to aid in the selection of pre-fabricated compression garments. Such compression garment fit information generated from shape description information provides marked benefits over more traditional compression garment fit information by providing better alignment between the person's body part or body area and the garment which is being fit. As a result, this methodology is receiving market acceptance in a short time.

However, there remains a need for further improvements in the generating compression garment fit information to better ensure that the intended amount of compression therapy is provided to the patient regardless of the characteristics of the tissue on the body part for which compression therapy is indicated. In particular, measurements generated from 3D imaging of a patient's body part from which measurements pertinent to determination of tissue compressibility of the subject patient body part would be desirable. It would further be beneficial to be able to derive tension circumference measurements from 3D imaging of a patient potentially in need of compression therapy. This disclosure provides these, and other, needed improvements.

SUMMARY OF THE DISCLOSURE

Aspects of the present disclosure are related to fitting of compression garments via compression garment fit information from 3D images taken of one or more body parts of a patient. In one aspect, among others, a method for generating compression garment fit information for a person comprises selecting a first body part on a person in need of compression therapy; acquiring 3D images of the first body part; processing the 3D images by a computing device, wherein the processing of the 3D images comprises deriving body part information for the first body part; and generating compression garment fit information from the derived body part information. The derived body part information can comprise tissue compressibility information; outer circumference information; and length information. In various aspects, the tissue compressibility information can be derived from each of a plurality of cross-sectional views of the first body part at different locations and is associated with body part tensioned circumferences at each location; for each body part location for which a cross-sectional view is generated, each of a body part outer circumference and a body part tensioned circumference can be provided; each body part tensioned circumference can be smaller than a corresponding outer body part circumference; and/or each of the body part tensioned circumferences and outer body part circumferences can be incorporated in the compression garment fit information.

In one or more aspects, the first body part can be a leg, and the plurality of cross-sectional views can comprise at least two cross-sectional views of the leg. At least one of the plurality of cross-sectional views can be generated at: a location proximate to a heel bottom and a location proximate to an ankle; or the location proximate to the ankle. At least one of the plurality of cross-sectional views can be generated at: a location proximate to ½ of a distance from the location proximate to the heel bottom and a location proximate to a popliteal region; a location proximate to ¾ of a distance from the location proximate to the ankle and the location proximate to the popliteal region; a location proximate to a bottom of a knee; the location proximate to the popliteal region; a location proximate to ½ of a distance from the location proximate to the popliteal region and a location proximate to a gluteal region; or the location proximate to the gluteal region. In other aspects, the first body part can be an arm, and the plurality of cross-sectional views can comprise at least two cross-sectional views of the arm. At least one of the plurality of cross-sectional views can be generated at: a location proximate to a palm at a base of a thumb; or a location proximate to a wrist region. At least one of the plurality of cross-sectional views can be generated at: a location proximate to ½ of a distance from the location proximate to the wrist region and a location proximate to an elbow region; the location proximate to the elbow region; a location proximate to ½ of a distance from the location proximate to the elbow region and a location proximate to an armpit region; or the location proximate to the armpit region.

In various aspects, the tissue compressibility information can be generated by: providing outer circumference information for at least two pairs of adjacent body part locations; and generating an adjacent body part outer circumference ratio for each of the at least two pairs of adjacent body part locations. The first body part can be a leg and the at least two pairs of adjacent leg locations can comprise one or more of: a first location proximate to a heel bottom and a second location proximate to an ankle; the first location proximate to the ankle and a second location proximate to ½ of a distance from the location proximate to the ankle and a popliteal area; a first location proximate to ½ of a distance from the location proximate to the ankle and a second location proximate to ¾ of a distance to a location proximate to a lower knee area; a first location proximate to the lower knee area and a second location proximate to the popliteal area; a first location proximate to the popliteal area and a second location proximate to ½ of a distance from a location proximate to the popliteal area and a gluteal area; a first location proximate to ½ of a distance from the location proximate to the popliteal area and a second location proximate to the gluteal area; or the location proximate to the gluteal region. The first body part can be an arm and the at least two pairs of adjacent arm locations can comprise one or more of: a location proximate to a palm at a base of a thumb and a location proximate to a wrist area; the location proximate to the wrist area and a location proximate to ½ of a distance from the location proximate to the wrist area and a location proximate to ½ of a distance between the wrist area and an elbow area; the location proximate to ½ of the distance between the wrist area and the elbow area; the location proximate to the wrist area and a location proximate to the elbow area; a location proximate to ½ of a distance from a location proximate to the elbow area and a location proximate to an armpit area; or the location proximate to the elbow area and the location proximate to the armpit area.

In one or more aspects, the compression garment fit information can be used to fabricate a custom-fabricated compression garment configured to provide compression therapy to the person when the garment is worn on the first body part. The compression garment fit information can be used in the selection of a pre-fabricated compression garment configured to provide compression therapy to the person when the garment is worn on the first body part. In some aspects, the first body part can be an arm; a compression garment fabricated from the compression garment fit information can be in a form of an arm sleeve and can incorporate a compression value of from 20 to 50 mm Hg; and the compression garment can be configured to apply the compression value to the body part when the compression garment is worn by the person. The first body part can be a leg; a compression garment fabricated from the compression garment fit information can be in a form of an leg sleeve and can incorporate a compression value of from 20 to 50 mm Hg; and the compression garment can be configured to apply the compression value to the body part when the compression garment is worn by the person.

In another aspect, a method for generating compression garment fit information for a person in need of compression therapy comprises: selecting first and second corresponding body parts in the person; acquiring 3D images of the first and second corresponding body parts; processing the 3D images by a computing device, wherein the processing of the 3D images comprises deriving for each of the first and second corresponding body parts; comparing tissue compressibility information for the first and second corresponding body parts, thereby generating information about a difference in tissue compressibility between each of a plurality of corresponding locations for the first and second corresponding body parts; and generating compression garment fit information for either or both of the first and second body parts.

The derived information can comprise the tissue compressibility information; outer circumference information; and length information. In various aspects, the tissue compressibility information can be derived from the processing of the 3D images as a plurality of cross-sectional views for different locations on the first and second corresponding body parts and can be associated with body part tensioned circumferences at each location; for each body part location on the first and second corresponding body parts for which a cross-sectional view is generated, an outer body circumference and a tensioned circumference can be generated; each body part tensioned circumference can be smaller than a corresponding outer body part circumference; and/or each of the body part tensioned circumferences and outer body part circumferences can be incorporated in the compression garment fit information.

In one or more aspects, the first and second corresponding body parts can comprise a first leg and a second leg and the plurality of cross-sectional views can comprise at least two cross-sectional views of each of the first and second legs. At least one of the plurality of cross-sectional views for each of the first and second legs can be generated at: a location proximate to a heel bottom and a location proximate to an ankle; or the location proximate to the ankle. At least one of the plurality of cross-sectional views of the first and second legs can be generated at: a location proximate to ½ of a distance from the location proximate to the heel bottom and a location proximate to a popliteal region; a location proximate to ¾ of a distance from the location proximate to the ankle and the location proximate to the popliteal region; a location proximate to a bottom of a knee; the location proximate to the popliteal region; a location proximate to ½ of a distance from the location proximate to the popliteal region and a location proximate to a gluteal region; or the location proximate to the gluteal region. The first and second corresponding body parts can be first and second arms, and the plurality of cross-sectional views can comprise at least two cross-sectional views of each of the first and second arms. At least one of the plurality of cross-sectional views can be generated at a location proximate to a palm at a base of a thumb; or a location proximate to a wrist region. At least one of the plurality of cross-sectional views can be generated at: a location proximate to ½ of a distance from the location proximate to the wrist region and a location proximate to an elbow region; the location proximate to the elbow region; a location proximate to ½ of a distance from the location proximate to the elbow region and an area proximate to an armpit region; or the area proximate to the armpit region.

In various aspects, the compression garment fit information can include a compression value configured to provide compression therapy to the person when the person is wearing a compression garment incorporating a tension value on either of the first or second corresponding body parts. The compression garment fit information can be used to fabricate a custom-fabricated compression garment configured to provide compression therapy to the person when the garment is worn by the person. The compression garment fit information can be used in the selection of a pre-fabricated compression garment configured to provide compression therapy to the person when the garment is worn by the person.

In one or more aspects, the first and second corresponding body parts can be first and second legs and the tissue compressibility information can be generated by: comparing outer circumferences for at least two pairs of adjacent body part locations for the first and second legs; and deriving an adjacent body part outer circumference ratio for each of the at least two pairs of adjacent body part locations. The at least two pairs of adjacent body part locations can comprise each of: a first location proximate to a heel bottom and a second location proximate to an ankle; a first location proximate to the ankle and a second location proximate to ½ of a distance from the location proximate to the ankle and a popliteal area; a first location proximate to ½ of a distance from the location proximate to the ankle and the popliteal area and a second location proximate to ¾ of a distance to a location proximate to the lower knee area; a first location proximate to the lower knee area and a second location proximate to a popliteal area; a first location proximate to the popliteal area and a second location proximate to ½ of a distance from a location proximate to a gluteal area; and/or a first location proximate to ½ of a distance from the location proximate to the popliteal area and a second location proximate to the gluteal area. The first and second corresponding body parts can be first and second arms and the tissue compressibility information can be generated by: comparing outer circumferences for at least two pairs of adjacent body part locations for the first and the second arms; and deriving an adjacent body part outer circumference ratio for each of the at least two pairs of adjacent body part locations. The at least two pairs of adjacent body part locations can comprise each of a first location proximate to a palm at a base of a thumb and a second location proximate to a wrist area; a first location proximate to the wrist area and a second location proximate to ½ of a distance from the location proximate to the wrist area and a location proximate to an elbow area; a first location proximate to ½ of a distance from the location proximate to the wrist area and a location proximate to the elbow area and a second location proximate to the elbow area; a first location proximate to the elbow area and a second location proximate to ½ of a distance between the elbow area and an armpit region; or a first location proximate to the elbow area and a second location proximate to the armpit region.

The identified embodiments and aspects are exemplary only and are therefore non-limiting. The details of one or more non-limiting embodiments of the disclosure are set forth in the accompanying drawings and the descriptions below. Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

FIGS. 4A and 4B illustrate an implementation of the disclosed methodology, in accordance with various embodiments of the present disclosure, in accordance with various embodiments of the present disclosure.

DETAILED DESCRIPTION OF THE DISCLOSURE

Figure 1:
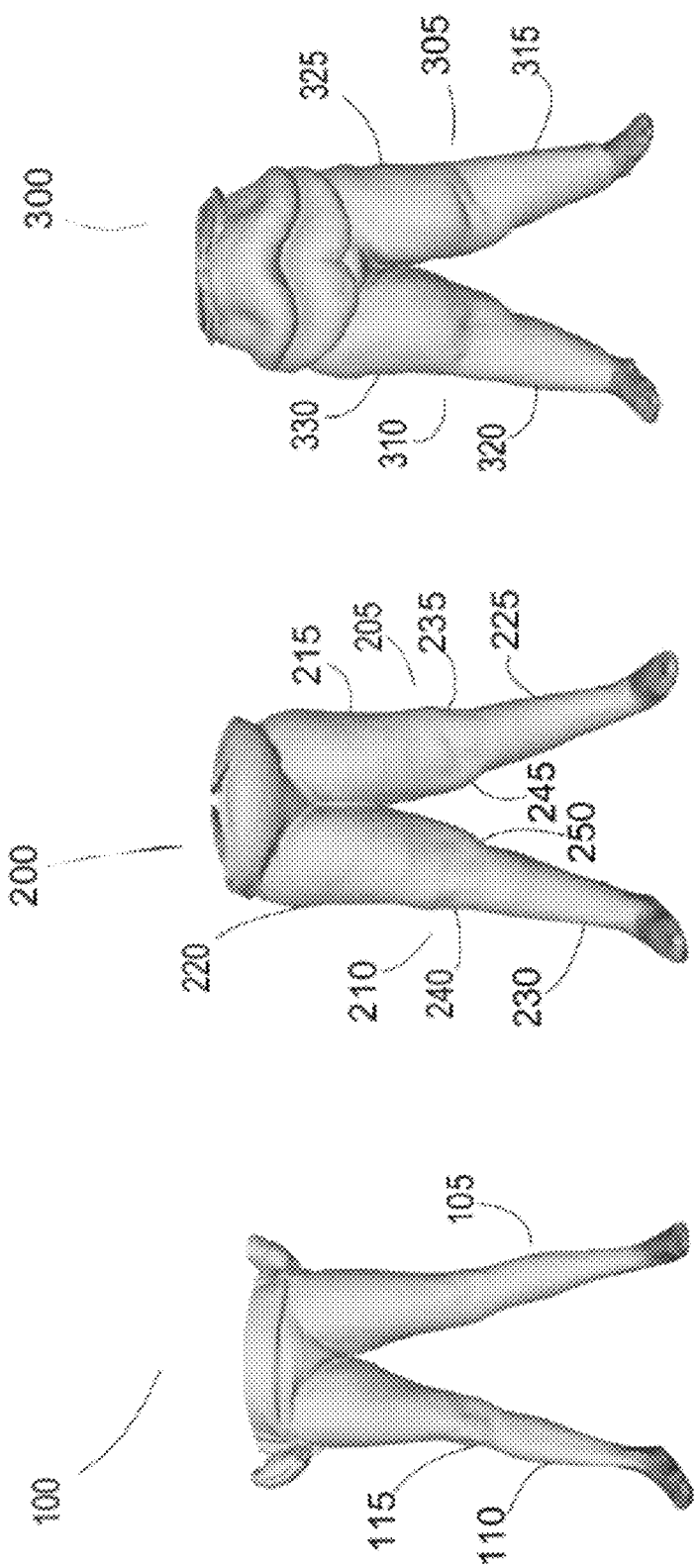
FIG. 1 depicts the legs of patients having different clinical presentations of edema, lymphedema and/or adipose tissue indications, in accordance with various embodiments of the present disclosure.

In the following detailed description, reference is made to the accompanying drawings, which form a part hereof, and within which are shown by way of illustration certain embodiments by which the subject matter of this disclosure may be practiced. It is to be understood that other embodiments may be utilized and structural changes may be made without departing from the scope of the disclosure. In other words, illustrative embodiments and aspects are described below. But it will of course be appreciated that in the development of any such actual embodiment, numerous implementation-specific decisions must be made to achieve the developers' specific goals, such as compliance with system-related and business-related constraints, which may vary from one implementation to another. Moreover, it will be appreciated that such development effort might be complex and time-consuming, but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and is also interpreted not to exclude additional features, limitations, aspects, etc.

The term "consisting essentially of" is meant to exclude any features that would change the basic and novel characteristics of the present disclosure, as claimed.

The term "about" is meant to account for variations due to experimental error. All measurements or numbers are implicitly understood to be modified by the word about, even if the measurement or number is not explicitly modified by the word about.

The term "substantially" (or alternatively "effectively") is meant to permit deviations from the descriptive term that don't negatively impact the intended purpose. Descriptive terms are implicitly understood to be modified by the word substantially, even if the term is not explicitly modified by the word substantially.

"Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as hypotonic fluid overload, which allows the movement of water into the intracellular space, or hypoproteinemia, which decreases the concentration of plasma proteins and permits the passage of fluid out of the blood vessels in to the tissue spaces. Other factors can include poor lymphatic drainage (known as "lymphedema"), conditions associated with an increased capillary pressure (e.g., excessive retention of salt and/or water), heart failure, and conditions associated with increased capillary pressure, such as inflammation (e.g., burns or other trauma).

The term "lymphedema" may include either primary or secondary lymphedema, the latter of which might also be term "acquired" lymphedema. Some forms of lymphedema can occur in morbidly obese patients, such as the condition known clinically as "Massively Localized Lymphedema." Lymphedema is a category of edema, although it is also characterized as a separately treatable indication, such as when it is a complication of breast cancer treatments in which lymph activity in patients is affected. As would be recognized, primary lymphedema is caused by abnormal development of the lymph system. Symptoms can be present at birth or may appear later in life. Secondary lymphedema is caused by damage to the lymphatic system. The lymphatic system may be disrupted, damaged or blocked by infection, injury, cancer, removal of lymph nodes, radiation to the affected area or scar tissue from radiation therapy or surgery. In some aspects, the present disclosure provides methods of detection of lymphedema that occurs as a result of removal or damage to lymph nodes that occurs after treatment of a patient for breast cancer.

"Compression garment" as used herein means garments that are constructed from elastic material and that are intended to apply pressure when stretched over the skin while being worn. Compression garments are worn over an area of the body where a therapeutic response (e.g., for treatment of lymphedema or swelling post-surgery etc.) or, when used in sports-related applications, enhanced recovery of a person after athletic assertion is intended. Typically, compression garments comprise one or more compression values that, when worn by a patient in need of treatment, are configured to apply an intended or prescribed level of compression therapy to the patient.

Compression garments are typically sized from a distal body part location to a proximal location, wherein "proximal" is in relation to the trunk, with more compression being applied at the distal location. Compression is applied from distal to proximal on the subject body part, for example, from the ankle to the knee or groin for a leg compression garment. The distal application of compression—or which is effectively a tension applied by the elasticity of the garment fabric and the circumference of the garment itself—aligns with the function of the lymph and vascular systems. In this regard, when a person is wearing a compression garment that is properly sized and fitted for that person's limb, trunk or extremity, etc. and incorporates a prescribed, defined, or selected amount of compression in the form of tension applied to the skin, such garments will apply a pressure to the skin and the area below with a goal to assist fluid flow in either or both of the patient's lymph or vascular system in the body part. Such increased fluid flow is intended to prevent or at least moderate damage that is associated with pour lymph and/or vascular circulation, as would be appreciated.

As would be appreciated, the circumference of a compression garment is smaller than the outer circumference of the body part on which the garment will be worn, such that the garment has a circumference that is different from that of the body part. When worn, the garment will be stretched to a circumference that allows the garment to fit the larger circumference of the body part, thus applying compression to the body part. The resulting level of compression applied to the body part is associated with the garment size as well as the amount of stretching capability incorporated into the fabric. Fabrics for compression garments are typically engineered with a stretchable composition that incorporates elastomeric material to achieve suitable stretch and compression.

The words "patient" and "person" are used interchangeably herein to describe someone who is indicated for wearing of a compression garment, wherein such compression garment can be fitted for the person according to the methodology of the disclosure.

In broad constructs, the disclosure herein provides methods and systems for generating compression garment fit information for a body part on a patient in need of or indicated for application of compression therapy on at least one body part. In this regard, the method comprises acquiring 3D images of a patient body part. The acquired 3D images are processed, where the processing comprises generating body part information for the subject patient body part. Such body part information includes outer circumference information, tissue compressibility information, and length information, and such information can be used to generate compression garment fit information for the subject body part. The patient can first be assessed by a clinician to diagnose the presence of edema/lymphedema, vascular symptoms or disease states or other indications associated with a diagnosis or condition where compression therapy with compression garments may be an appropriate treatment option.

U.S. Pat. Nos. 10,045,581 and 10,251,438 (the "'581 Patent" and "'438 Patent," respectively), previously incorporated by reference in their entireties, provide detailed explanation of the generation and use of shape description information for a patient body part in need of treatment with compression therapy, where that therapy can be provided by compression garments configured with an indicated compression level. In summary, and as disclosed in the referenced '581 and '438 Patents, shape description provides information about the unique aspects of the outer shape of the body part as derived from 3D images thereof. Such shape description information allows an outer circumference of the subject patient body part to be described accurately in geometric/numerical form. As disclosed by the '581 Patent and the related '438 Patent, such shape description information can allow the outer circumference of all or part of a patient body part of interest to be accurately defined which, in turn, provides information about the true external shape of the patient body part or body area, or "morphology," to be provided.

The inventors herein have determined that while the shape description information generated from the methodology of the '581 and '438 Patents can be beneficial in the fitting of compression garments for some patients in need thereof, in use, for some patients, the generation of a proxy for the tensioned tape measurement that is associated with the underlying tissue composition at a plurality of locations on the body part can better ensure that the amount of compression applied to a subject patient body part by a compression garment is suitably configured to provide the intended amount of compression thereto. The imaging methods of the '581 and '438 Patents can also be used to obtain images from which tissue compressibility information can be derived, as further set out herein.

Some patients can have a degree of body part distortion that can affect the amount of compression applied from the compression garment to the body part, as discussed further herein. Such body part distortion can be a result of a patient being symptomatic for edema/lymphedema and/or due to excess adipose tissue being present. Such limb distortion will typically result in the body part presenting with more compressible tissue when a tape measurement method of fitting compression garments is utilized. Thus, for some patient body parts in need of compression therapy, the amount of pressure intended to be applied by the compression garment is not fully transmitted to the patient's lymph or vascular system. In short, such compressible tissue may "absorb" or dissipate (e.g., will be less likely to transfer an applied force) at least some of the applied compression, and the applied compression may not effectively act on the underlying lymph or vascular system.

With the prior art tape measurement method, this differential between applied pressure (from the compression garment) and received pressure (by the patient's lymph or vascular system) can be managed by defining a compression garment fit that takes into account a greater compressibility of the body part according to a formula that is incorporated into compression garment fit instructions. While the formulas for compression garment fit description can vary among manufacturers, generally, compressibility of the body part as found by tape measurement will be incorporated into compression garment fit information that is used to fabricate a custom compression garment or in the selection of a prefabricated compression garment. In some implementations, compression garment fit information for a limb that is more "compressible" will incorporate an enhanced level of elasticity so as to make the garment "tighter" when worn. Such tightness can minimize the effect of the tissue compressibility to better transfer applied compression to the limb to the vascular or lymph system of the body part.

In some patients, it follows that for compression therapy to be effective, additional information may be needed over that provided from outer shape description information as in the '581 and '438 Patents. These patients may present with an outer body part circumference derived from shape description information, such as that described in the referenced patents, that indicates fabrication or selection of a first compression garment having one compression value but, in use, that selected compression garment will not be suitable to apply the intended amount of compression. Similarly, a patient with fibrotic tissue may be fitted with compression garment that is "too tight" due to the lesser compressibility of such tissue.

In accordance with the present disclosure, for tissue that presents as "more compressible," a tensioned circumference measurement for the compression garment can better ensure that an effective amount of compression can be imparted to the subject body part as intended for an applied compression therapy. Such substitutes for tensioned skin circumference measurements can be derived from the 3D images of the patient body part.

In a first implementation, the disclosure provides methods and systems generating compression garment fit information for an identified or selected person, for example, a patient, where the identified or selected person is in need of compression therapy. The need for compression can be indicated by a clinician or can be self-identified by the patient. A first body part can be identified in the patient, and 3D imaging of the body part is acquired as discussed herein. The acquired 3D images can be processed to derive tissue compressibility information, outer skin circumference information, and length information for the identified body part. The derived tissue compressibility information can serve as a substitute for tape measurement circumferences taken under tension at the subject locations on the body part. As such, the present disclosure allows 3D imaging information to be used to generate compression garment fit information for the patient where the fit information also takes into account any tissue compressibility characteristics for the subject body part. As noted, while such tissue compressibility information has been included in compression garment fit information generated from tape measurements in the prior art, such information has not previously been available using 3D imaging methods. The present disclosure allows compressibility information to be generated directly from imaging data and without use of a tape measure.

As indicated previously, existing methods of generating compression garment fit information from 3D images focus on the outer circumference information for which a compression garment size can be matched to fit a person. An improvement herein is provided by the derivation of tissue compressibility information from the 3D images, such that at least two measurements for each body part location can be derived for incorporation into garment fit information for the patient. Used with body part length information, such at least two measurements can be used to generate compression garment fit information suitable to impart a defined compression level to the patient when a garment having the fit information is worn by the patient on the body part.

To illustrate this concept, FIG. 1 provides images of 3 different people taken from the fronts thereof. Patient 100 has left leg 105 and right leg 110. Differences in the shapes of 105 and 110 can be observed, with 105 being visibly larger and shaped differently than 110. In this regard, left leg 105 has visibly detectable differences in curvature, cross-section, axial contour patterns. In contrast, right leg 110 can be characterized as having "regular compression," according in both the cross-sectional and axial tissue compressibility characterizations described herein. In other words, left leg 105 might be termed "distorted" over right leg 110. Clinically, the difference in size and shape in patient 100 were determined as being due to early stage edema being diagnosed in left leg 105, whereas right leg 110 is non-symptomatic of either edema, lymphedema or an abundance of adipose tissue. Further, if measured according to the tape measurement method, there would a difference between the outer circumference measurement and the circumference measurement under tension of legs 105 and 110 when a plurality of measurements for each type of circumference were generated at each location. Such differences would normally be included in a formula provided for selection of a compression garment via tape measurement, as discussed above. As discussed hereinafter in relation to FIG. 2, the methods and systems herein, such circumference differences, and the associated need for compression garments that take into account the tissue compressibility for a leg such as 105 due, at least in part, to the presence of early stage edema therein, can be derivable from processing of the 3D images.

Again referring to FIG. 1, patient 200 has left leg 205 and right leg 210. Clinically, patient 200 has been diagnosed with fibrosis in both legs 205 and 210, adipose tissue deposition in thighs 215 and 220. Visually, the lower leg portions 225 and 230 are indicated by changes in circularity, curvature, axial contour patterns that are cognizant with fibrosis diagnoses. Moreover, knees 235 and 240 visibly exhibit less definition than those of a healthy individual, such as that of knee 115 in patient 100. Bottom portions 245 and 250 of thighs 215 and 220 show signs of tissue overhang associated with adipose deposition. Body part circumference information generated according to the methodology herein will indicate that a tissue compressibility measurement incorporated into compression garment fit information will take into account the compressibility of the tissue thereof to ensure that the intended compression therapy is provided to patient 200, in addition to a body part information that addresses the outer circumference of legs 205 and 210.

As further illustration, patient 300 clinically exhibits an advanced case of bilateral lymphedema. Legs 305 and 310 are dearly visibly large at lower portions 315 and 320, but they exhibit markedly different characteristics than legs 205 and 210 of patient 200. In this regard, the curvature and axial contour pattern are associated with high-compressibility tissue, rather than fibrotic tissue, as in patient 200. Upper legs 325 and 330 can also be inferred to have the characteristics of high-compressibility tissue. Shape description information generated according to the methodology herein will indicate that a tensioned circumference incorporated into a compression garment for legs 305 and/or 310 will need to take into account the compressibility of the tissue thereof to ensure that the intended compression therapy is provided to patient 300.

The methodology herein can be substantially independent from any other information known about the subject such as gender, age, or disease status. That is, the patient for which the compression garment fit information is being generated need not have been clinically diagnosed, such that the compression garment fit information can be generated directly from the digital images of the person. In this regard, tissue compressibility information can be derived solely from the digital images of the body part. Alternatively, information generated from the specific patient (age, clinical presentation, clinical diagnoses, etc.) can be incorporated in the process to inform the compression garment fit information to provide additional useful information.

When a determination is made that the tissue of the subject body part is "compressible," a compression garment having a smaller circumference and/or different elasticity characteristics—can be identified vs. that which would be indicated from a shape description that generates only an outer circumference. For example, if processing of 3D images of the subject body part indicates that the tissue is "compressible," a garment having at least about an about 3% or 5% or 7% or 10% smaller circumference than would be indicated from 3D images, such as shape description information, that takes into account only outer circumference information for the body part. The additional tension on the body part, as provided by additional compression of the body part imparted by the garment, can be incorporated into compression garment fit information to allow fabrication of (for a custom garment) or selection of (for a pre-fabricated garment) to better ensure that the intended amount of compression therapy is provided to the patient irrespective of the compressibility—that is, compositional characteristics—of her tissue. For fibrotic tissue, compression garment fit information may indicate that less tension should be indicated for such patient.

As would be appreciated, such additional compression can also be included by defining garment fit parameters to generate a garment that fits "tighter" on the body part, where such "tightness" is dictated by the elastic characteristics of the garment, as well as the circumferential dimensions, incorporated into the manufacture thereof. In use, it will be "tighter" on the patient's body part, so that, when worn, the garment will apply the intended amount of compression therapy even though the tissue of the body part may absorb or dissipate some of the applied compression.

Differences between the body parts of a person indicated for compression garment fitting can be generated by comparing body part information for each of corresponding body parts of the patient, such as both legs or both arms. In this regard, 3D images can be generated of each body part according the methodology herein, and the tissue compressibility information and outer circumference for each relevant body part location can independently be generated. The body part information includes both outer circumference and tissue compressibility information for a plurality of locations on each of the body parts, where the body part information can be incorporated into compression garment fit information for a garment to be worn by the patient on the subject body part. As would be appreciated, body part length information is also relevant to compression garment fit information and can also be derived from the 3D images.

Figure 2:
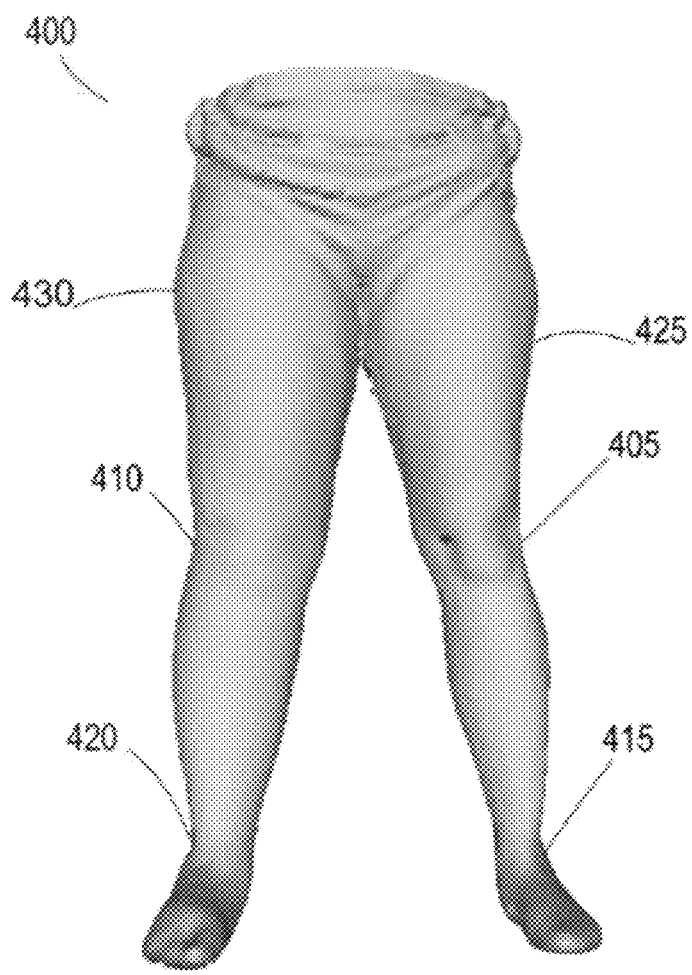
FIG. 2 depicts the legs of a patient with different clinical presentations of edema, lymphedema and/or adipose tissue indications, in accordance with various embodiments of the present disclosure.

Referring to FIG. 2, which shows legs of a patient 400, tissue compressibility information derived from the 3D images of patient legs 405 (left leg) and 410 (right leg) would indicate that edema-symptomatic leg 410 would benefit from a compression garment that generated greater tension—that is, was "tighter"—vs. a garment suited for "regular compression" leg 405, at least because ankle 420 would absorb or dissipate some of the tension applied by a compression garment worn thereon, whereas ankle 410 would not. Thus, compression garment fit information for leg 410 can include additional tension to manage the loss of some of the tension as a result of the compressive tissue on leg 410. For example, the tensioned circumference for a compression garment for leg 410 can have a value that is 3%, 5% or 10% less than the tensioned circumference of a compression garment for leg 405. This smaller tensioned circumference in the compression garment would provide for a "tighter" fit on leg 410, but such fit should not result in pinching or feel overly tight because at least some of the "tightness" will be absorbed or dissipated by the tissue.

In addition to the differences between legs 405 and 410 (or other body parts), there can also be differences in tissue compressibility within a single body part. Referring again to FIG. 2, in both left leg 405 and right leg 410, left ankle 415 and right ankle 420 will almost always be less compressive than the top of each of respective thighs 425 and 430, at least because the former will be more bony than the latter. The inventors herein have determined that body part information can be derived from the 3D images of a body part of interest, where such body information can provide a tissue compressibility of all or part of a body part indicated for compression garment fitting. This can allow people with varying amounts of adipose tissue who nonetheless may not be obviously symptomatic of edema/lymphedema to attain improved fitting for compression garments.

In various implementations, tissue compressibility information can be derived or generated from 3D images of the subject body part. The methodologies for generating the digital images are described in detail in the '581 and '482 Patents, previously incorporated by reference in their entireties.

Figures 3A, 3B:
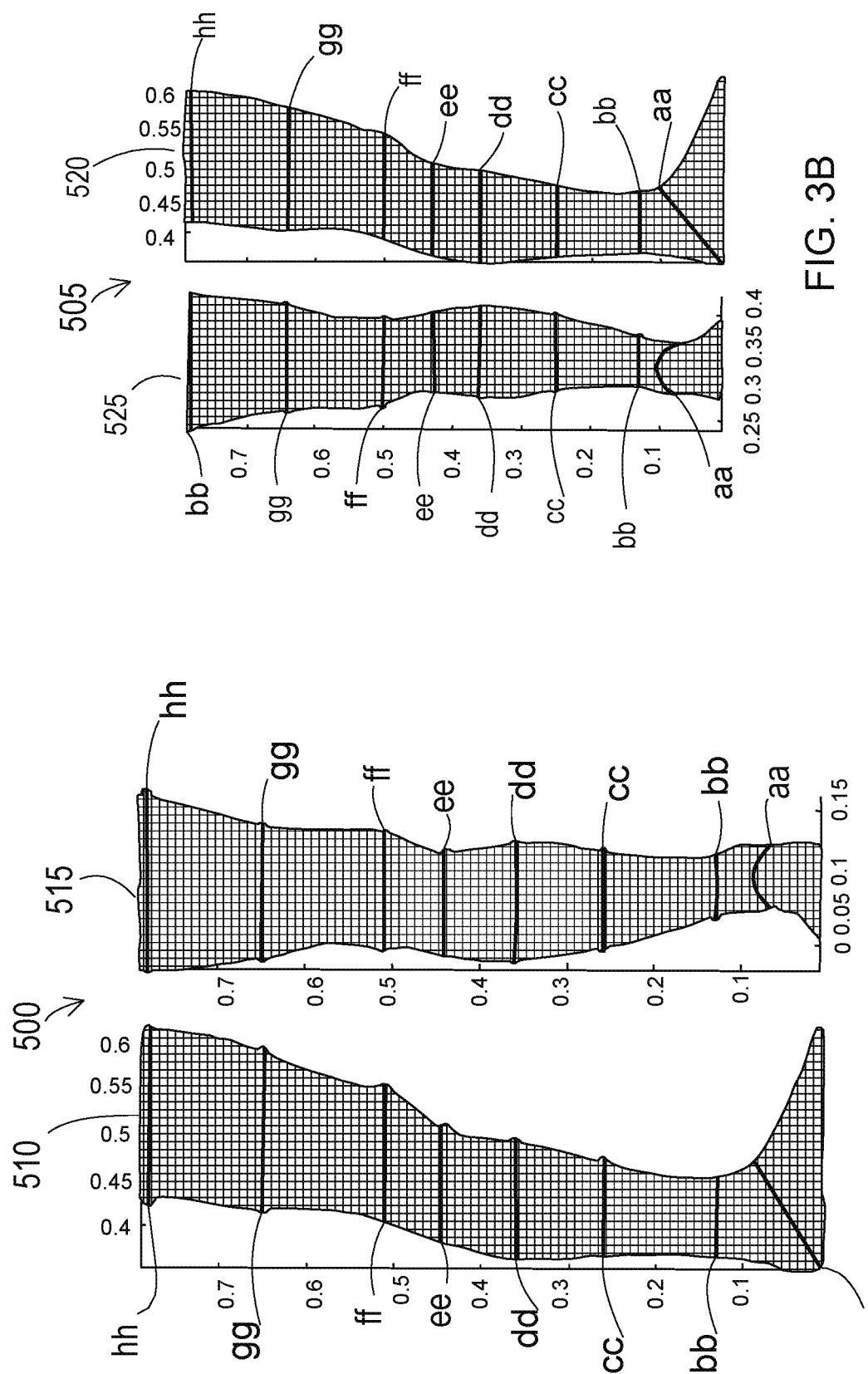
FIGS. 3A and 3B illustrate various body part locations where shape description information can be generated according to the disclosed methodology, in accordance with various embodiments of the present disclosure.

As shown in FIG. 3A (right leg 500) and FIG. 3B (left leg 505) the 3D images of the legs, here shown as illustrations derived from 3D images of a patient's leg for clarity, can be generated for the outer side 510 and front side 515 (or back side) of the right leg 500 and the inner side 520 and front side 525 (or back side) of the left leg 505 at the locations described below in relation to FIGS. 4A and 4B. To maintain consistency within and between individual imaging events for each patient and among patients, an invariant scale can be included with the images to ensure that the imaging locations remain consistent.

In FIGS. 3A and 3B the various leg locations where shape description information can be derived are shown for leg views 500, 505, 510 and 515. Such locations can include:
 i. a location proximate to a heel bottom and a location proximate to an ankle (aa);
 ii. a location proximate to the ankle (bb);
 iii. a location proximate to ½ of a distance from the area proximate to the heel bottom and a location proximate to a popliteal region, i.e., the lower calf (cc);
 iv. a location proximate to ¾ of a distance from the area proximate to the ankle and the location proximate to the popliteal region, i.e., the mid-point of the calf (dd);
 v. a location proximate to a bottom of a knee (ee);
 vi. a location proximate to the popliteal region (ff);
 vii. a location proximate to ½ of a distance from the location proximate to the popliteal region and a location proximate to a gluteal region, i.e., the mid-thigh (gg); and
 viii. a location proximate to the gluteal region (hh).

It should be noted that anatomical variations within and among patients can also be accounted for in various implementations. The use of the invariant scale mentioned previously can allow a patient to be measured consistently at the body part locations listed herein, or at other locations, as appropriate in a situation. Measurements between patients can also be facilitated by such invariant scale.

Referring to FIGS. 4A and 4B, two circumference measurements derivable from shape description information are illustrated for ankle location bb of leg views 500 and 505 in FIG. 4A. In this regard, as shown in FIG. 4B circumference bb1 indicates an outer body part circumference and bb2 indicates a tensioned circumference, where the difference between bb1 and bb2 is associated with the tissue compressibility at that body part location, namely bb.

Figure 5B:
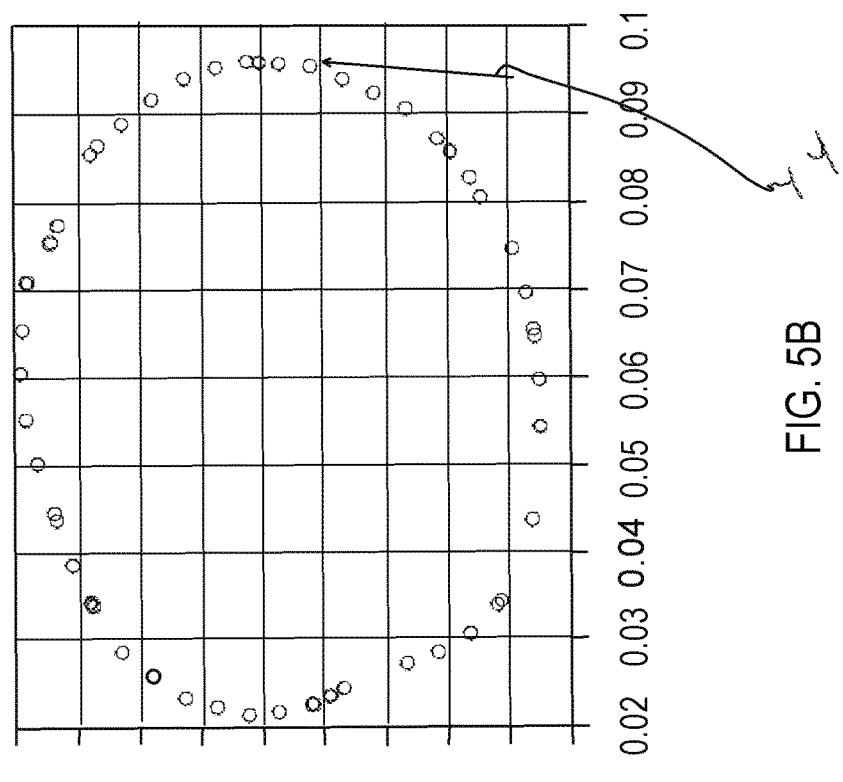
FIGS. 5A and 5B illustrate shape descriptions for two different ankle areas having different shape descriptions, in accordance with various embodiments of the present disclosure.
Figure 5A:
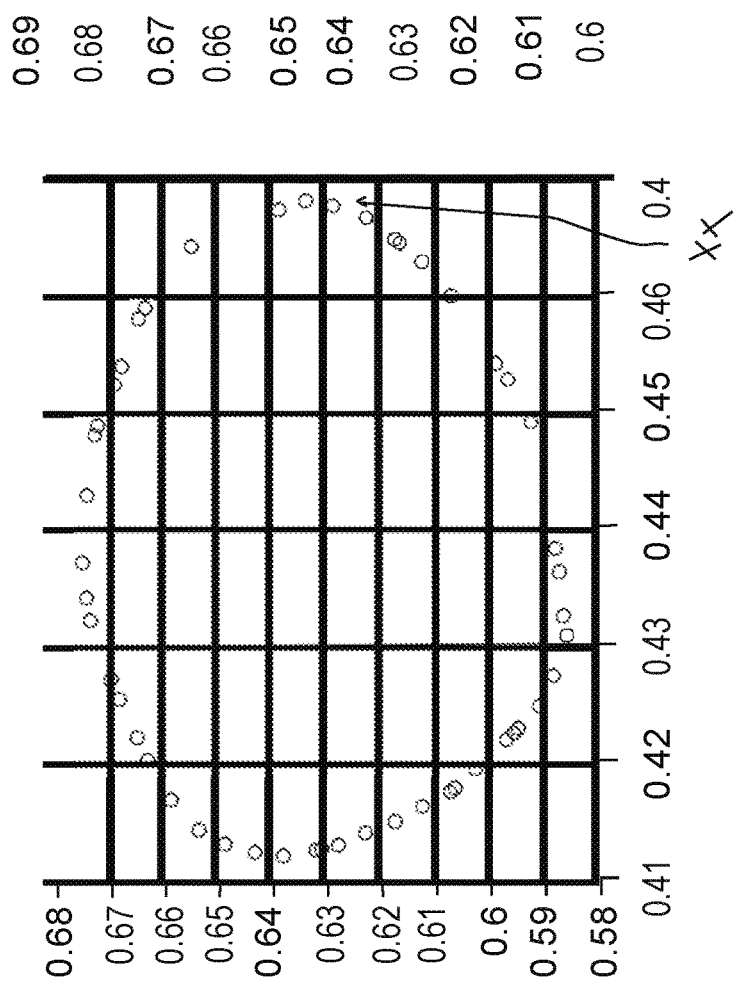

Cross-sectional views can be useful for deriving tissue compressibility information. As illustrated in FIGS. 5A and 5B, which are cross-sectional views for patient 400 at left ankle 415 in FIG. 5A and right ankle 420 in FIG. 5B, a "regular" compression—that is, a body part having a location that is not symptomatic of an indication that manifests as compressible tissue—can generate a shape description that presents as less circular than a corresponding body part that is symptomatic. In this regard, XX depicts a shape that is more indicative of an Achilles tendon that is visibly prominent from the imaging information shown in FIG. 5A. A compression garment indicated for this area of patient 400 would impart the intended amount of compression at least because the non-circularity of the shape indicates that ankle 415 does not include compressible tissue that would have a tendency to absorb or dissipate the compression applied by a compression garment. In contrast, ankle 420 in FIG. 5B exhibits more circularity YY at the Achilles tendon region. A compression garment intended for wearing at ankle 420 would therefore need to apply a greater amount of compression at that location at least because of the tissue compressibility as shown by the lack of a visible Achilles tendon visible in the cross-sectional view. In other words, cross-sectional views in FIGS. 5A and 5B can be translated into information from which tissue compressibility information can be derived.

As would be appreciated, the tissue compressibility within the same body part and between two body parts on the same patient can vary, and such variability and the values associated therewith can be incorporated in compression garment fit information for that person. The 3D images can be processed to generate outer circumference information from the shape description information as set out in the '581 and '438 Patents. As discussed therein, within a single person's body part, there can be morphology differences. When being treated with compression therapy via compression garments, it can be beneficial to accommodate such body morphologies in a compression garment fitted specifically for that body part. Moreover, it can be beneficial to generate compression garment fit information without having to go through the cumbersome process of tape measurement by a trained fitter. Generation of both the outer body part circumference and tissue compressibility information via 3D imaging can facilitate such compression garment fitting.

As noted, body part length information can be incorporated into the compression garment fit information, where such fit information can be derived from the digital images. For custom compression garments, an exact or nearly exact length of each portion of the body part can be incorporated into custom compression garment fit information. For prefabricated garments, the body part length information can be used to select an appropriate size for the patient, such as "short," "regular," "long," and "extra-long," or the like.

Although not illustrated, the body part indicated for fitting can be an arm. In this regard, when the body part indicated for fitting with compression garment is a leg, a plurality of locations for the cross-sectional views can be selected:
 i. a location proximate to the palm at the base of the thumb; or
 ii. a location proximate to the wrist region;
 iii. a location proximate to ½ of the distance from the area proximate to the wrist and an area proximate to an elbow region i.e., the midpoint of the forearm;
 iv. a location proximate to the elbow region;
 v. a location proximate to ½ of the distance from the location proximate to the elbow region and the area proximate to an armpit region, i.e., the midpoint of the upper arm; and
 vi. the area proximate to the armpit region.

Again, length information can further be derived for the arm from the body part information. Such information can be in the form of actual length information, or generally, as in accordance with general sizing in "small," "medium," "large," "extra-large" or the like.

In one implementation, the tissue compressibility information can be derived from cross-sectional view information derived from the 3D images. A plurality of cross-sectional area views can be generated for the body part, for example, at the locations indicated above in FIGS. 3A and 3B, where each of the plurality is generated at a location on the body part of interest. While any number and type of cross-sectional locational views can be generated, it can be beneficial for at least some of the plurality to conform to locations that are used in the sizing of compression garments conventionally, where such locations are indicated above.

As would be appreciated, for a leg compression garment, the relevant lowest body part location can be defined by the distal location defined by either or both of locations aa or bb, with at least one set of tissue compressibility and outer circumference information being generated at a location above these distal locations. At least two sets of tissue compressibility and outer circumference information can be generated at a first and second location on the leg (or arm), or three or more.

To this end, because compression values for a patient are generated to provide compression therapy to improve lymph or vascular flow, at least one reference point for the application of compression therapy can be at a lower or distal location on the patient body part. For a leg, the lower location can be the ankle location (i.e., bb) or, for some patients, the location that spans the bottom of the foot to the bottom of the ankle location (i.e., aa). For leg compression therapy, compression garment fit information will be generated so that the lower portion of the compression garment (e.g., aa or bb) will suitably apply a compression value that is from about 20 mm Hg to about 50 mm Hg as applied by the compression garment via the elasticity incorporated therein. To generate appropriate compression garment fit information for other locations along the body part, additional tissue compressibility and outer circumference information can be derived. For example, tissue compressibility and outer circumference information can be generated for at two additional leg locations, where a topmost leg location on which the compression garment is fit is one of the additional body part locations. For example, a compression garment in the form of a sock may only be worn up to the calf location, which is the location that is approximately ¾ of the distance between the ankle location (bb) and the popliteal (ee) on the patient's leg. A full leg compression garment may extend from the location below the ankle (aa) to the groin region (hh), with other body part locations in between those locations potentially being relevant to the compression garment fit information such that tissue compressibility and outer circumference information is generated for at least one location in between the first and second ends of the compression garment as it is to be worn on the body part of the patient. As would be appreciated, at least 3 sets of tissue compressibility and outer circumference information will allow the generation of both outer circumference and tissue compressibility characterizations for each body part. In some implementations, such information can be generated for 3 or more locations on the body part. Compression garment fit information used in the fabrication of custom garments can include more circumference measurements, whereas compression garment fit information for use with pre-fabricated compression garments may not benefit from more than 3 or 4 circumference values.

When the body part for fitting with a compression garment is an arm, a plurality of cross-sectional views of the arm are also generated, with at least the first end and second end of the garment as fitted and a middle location thereof being used to generate outer circumference and tissue compressibility measurements. For example, an arm sleeve extending to the armpit that does not include the hand will be measured from the wrist location to the armpit, with at least one cross-sectional view being generated for a location between that location, namely the elbow. For an arm sleeve that extends to the hand, a cross-sectional view of the location around the palm at the base of the thumb can be generated, and outer circumference and tissue compressibility information being derivable therefrom, as well at the upper fit location (e.g., the forearm, elbow, or armpit). At least one additional cross-sectional view can be generated, or even more, to improve the compression garment fit information quality.

In a further implementation, tissue compressibility information can be derived from 3D image information associated with an axial length of the patient body part. In this regard, tissue compressibility information can be derived from axial shape description for the subject body part, where "axial" refers to a length of the body part of interest. By "axial" it is meant that at least some of the outer surface of a body part from body part location to body part location is generated. In such an implementation, the perspective of tissue compressibility is distal-proximal along a body part, not circumferential, as with the cross-sectional view implementation discussed herein.

Referring again to FIG. 1 and FIG. 2, one can observe the shapes along the various legs. By evaluating the external surface shape along an axial length, tissue compressibility along the axial length can be derived, and combined with outer circumference derived from the images.

Axial contour patterns as derivable from the 3D images can also be used to develop compression garment fit information. In this regard, the contour, or lack thereof, observed along an outer area of the body part can be informative. The contour derived from 3D imaging of the body part along an axial length can therefore provide information about the tissue compressibility.

As discussed previously, for a patient having healthy tissue composition, a leg or arm will exhibit defined contour between body part locations. For example, a person with healthy tissue composition in her lower leg will exhibit an ankle location that is smaller than her calf area, and a calf area that is larger than her knee area. Similarly, her knee area will be smaller than her thigh area. In contrast, a person who is symptomatic of edema/lymphedema and/or who presents with significant amounts of adipose tissue, will exhibit lesser differentiation between body part locations. Colloquially, the leg may appear more "trunk-like" or "cylindrical," as opposed to having a visible contouring along an axial length thereof. Such lack of contouring can be observed from 3D imaging information taken along a length of the lower part of a person's leg or along the upper portion of a person's leg or both. While the tissue compressibility can be due to either or both of edema/lymphedema or excess adipose tissue, in either case, an application of compression therapy to the patient may not be effective as at least some of the compressible tissue will absorb or dissipate the compression applied by the garment. In order to provide the intended amount of compression therapy, the patient may benefit from use of a compression garment that exhibits a tensioned circumference that is smaller than the outer circumference obtained from compression garment fit information that is generated only of the body part outer circumference. For example, if the goal is to apply 20 mm Hg to an ankle location, the tensioned circumference for a compression garment may need to be smaller to account for the absorption or dissipation caused by the compressible tissue. As such, the compression value applied by the compression garment would need to be increased so as to provide the desired amount of compression therapy to the body part.

While the example of lower leg has been shown, other contour differentials between body part locations can be used in the axial methodology. A number of adjacent body part locations can be compared to derive a ratio between each adjacent body part circumference. Such comparisons can be between a plurality of the following pairs when the body part is a leg (location as shown in FIGS. 3A and 3B):
  a. a first location proximate to a heel bottom (aa) and a location proximate to an ankle and a second location proximate to an ankle (bb);
  b. a first location proximate to the ankle (bb) and a second location proximate to ½ of a distance from the area proximate to the ankle and a popliteal area (cc);
  c. a first location proximate to ½ of a distance from the location proximate to the ankle (cc) and a second location proximate to ¾ of the distance to an area proximate to the lower knee area (dd);
  d. a first area proximate to the lower knee area (dd) and a second location proximate to a popliteal area (ff);
  e. a first location proximate to a popliteal area (ff) and a second location proximate to ½ of a distance from the area proximate to gluteal area (gg); and
  f. a first location proximate to ½ of a distance from the location proximate to the popliteal area (gg) and a second location proximate to a gluteal area (hh).

Although not illustrated, outer circumference ratios can also be derived from digital images of an arm. In this implementation, the plurality of cross-sectional views can be generated from a plurality of pairs comprising:
  a. a first location proximate to the palm at the base of the thumb and second location proximate to a wrist area or region;
  b. a first location proximate to the wrist area or region and a second location proximate to ½ of the distance from the area proximate to the wrist area or region and an area proximate to an elbow area;
  c. a first location proximate to ½ of the distance from the area proximate to the wrist area and an area proximate to the elbow area and a second location proximate to the elbow area;
  d. a first location proximate to the elbow area and a second location proximate to the area ½ of the distance between the elbow area and an armpit region; and
  e. a first location proximate to the elbow area and a second location proximate to an armpit region.

A plurality of outer circumference ratios can be generated from the 3D images, where the plurality can comprise 3 or more. Since the compression garment fit information can be generated for any location on the body part, any two location pairs can be compared to generate a ratio between circumference. However, it can be useful to use the anatomical landmarks generally used to for body part identification, as such landmarks are set out above.

Body part information generated from processing of the 3D images has been determined to allow measurable differences to be detected along a body part length, both partial and full, between a single patient for a first and a second body part (e.g., an arm:arm or leg:leg) and within a single patient during longitudinal measurements of a single body part.

Figure 6:
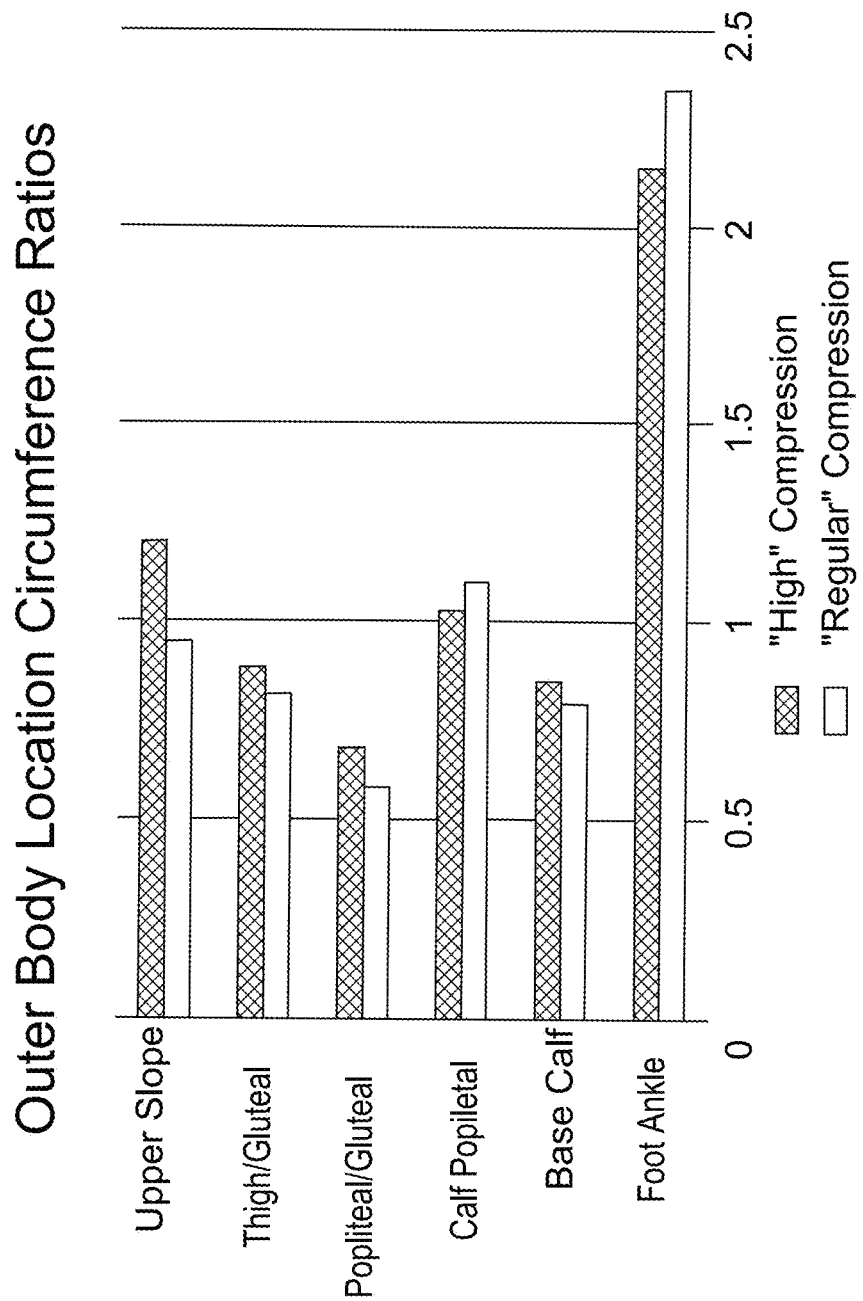
FIG. 6 provides body part circumference ratios for various adjacent leg part location pairs, in accordance with various embodiments of the present disclosure.

FIG. 6 illustrates outer circumference ratios for adjacent parts of body parts, where the ratios are derived from body part information that includes outer circumference information for each body part location. Differences in anatomic shape profile are highly evident between normal compression and high compression legs. This collection of anatomic regions is representative of where the greatest shape change occurs as tissue compression changes within legs. As shown, tissue compression can also vary regionally within a leg, which is partly dictated by the anatomy (bony regions are always less compressible than fleshy regions), and partly variable and measurable. The inventors have determined that one of the most common patterns along the length of a body part such as a leg is that "normal compression" legs have more contour (especially around the joints) than the higher compression legs. Thus, it has been determined that the contour along the axial length of a body part can be used to derive tissue compressibility information to generate compression garment fit information for a person who is symptomatic of an indication where tissue composition or characteristics where compression garment therapy may be less effective due to absorption and/or dissipation of an applied compression.

Figure 7:
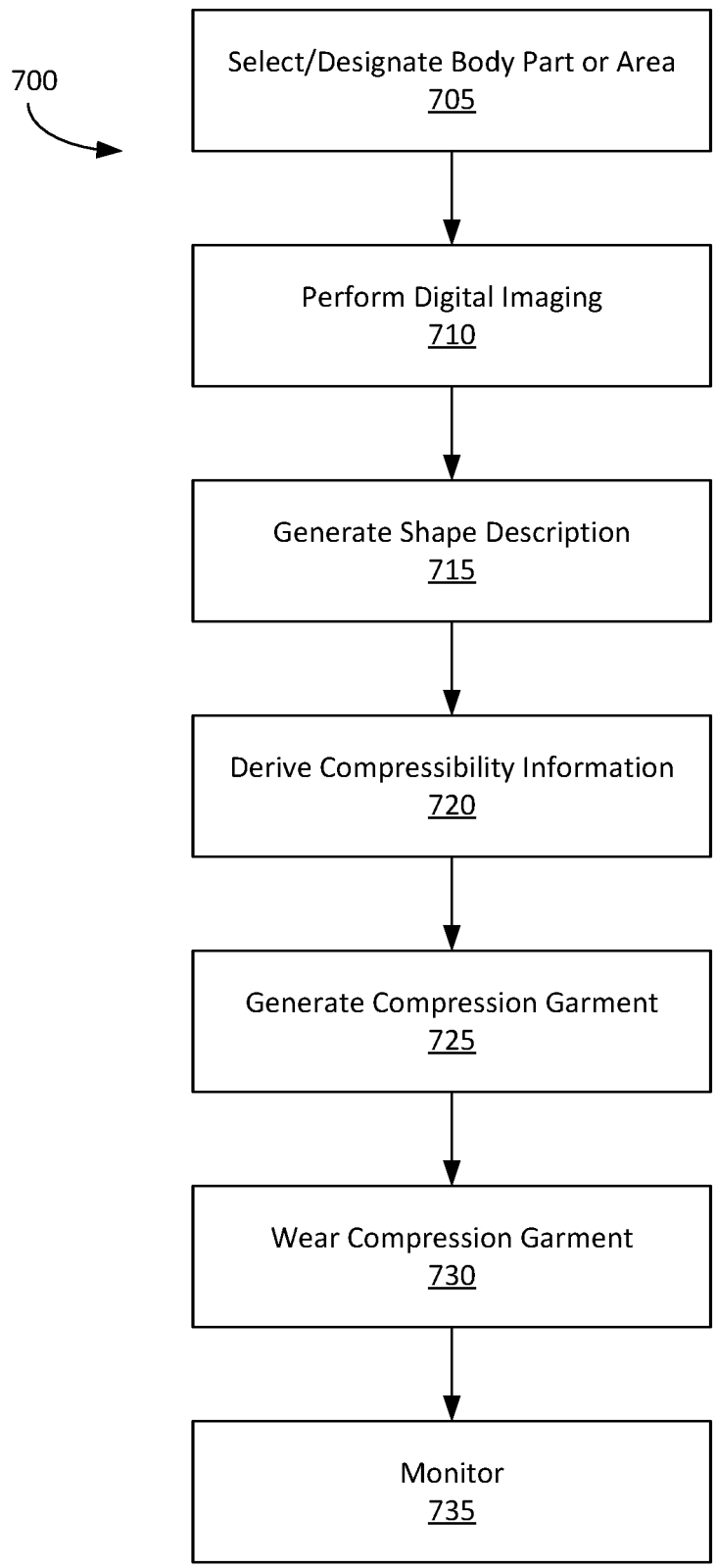
FIG. 7 illustrates an example of the derivation of body part description information, in accordance with various embodiments of the present disclosure.

Referring now to FIG. 7, shown is an example of the derivation or determination of the body part description information from 3D images of a body part. In various implementations, compression garment fit information for a subject body part can comprise outer circumference measurements, tension circumference, and length. In the example of FIG. 7, the process 700 begins at 705, where a body part of or body area of a patient in need of treatment is selected or designated for imaging. In 710, digital imaging of the selected body part or body area is performed to acquire the 3D images, which can be rendered on a screen viewable by the operator in the form of, e.g., a depth map. Digital images of the body part or body area of interest can be acquired according to the methodology of the '581 and '438 Patents, previously incorporated by reference in their entireties, or other appropriate process. Such acquired 3D images can be processed in 715 to generate a shape description of the selected body part or body area including outer circumference measurements.

In 715, body part outer circumference information can be derived via various imaging methodologies, for example, that set out in '581 and '438 Patents, or other processes, such as the four-sided imaging technique such as disclosed in US Patent Application Publication No US20160235354, the disclosure of which is hereby incorporated by reference in its entirety. The "shape description" methodology in the '581 and '438 Patents provides a comprehensive methodology that is capable of deriving morphology information for the subject body part (among other things), however, less detailed body part information can also be useful, for example, when the shape of the subject body part location is clearly discernible from the images, such as in the methodology of the referenced patent publication. Similarly, length information can be derived via the images generated from the methodology of the '581 and '438 patents, or other suitable methodologies. As would be appreciated, the length of the entireties of a subject body part (e.g., groin to foot, armpit to wrist), or sections thereof (e.g., knee to foot, elbow to wrist) can appropriately be a generalized length (e.g., small, medium, long, etc.), whereas the circumference information derived from the images should be more closely aligned with the actual circumference of each of the relevant locations of the subject body part at least because of the nature of an applied compression therapy.

Tissue compressibility information can then be derived from the imaging of the subject body part at 720. Tension circumference can be derived at 720 from the combination of the generated body part outer circumference and tissue compressibility information. As used herein, "tissue compressibility" is a feature of the subject body part comprising the compressibility characteristics of human tissue, where such "compressibility" is the ability of the subject body part or body part location to "absorb" or dissipate tension applied by a compression garment configured to impart compression to the underlying lymph and/or venous system of a patient wearing the compression garment on her body part. Tissue compressibility can, in turn, be derived from a generated body part tension factor, a geometric information modifier, and available patient information, as such are defined below. In some implementations, either or both of the geometric information modifier and the available patient information can be optional in that they need not be included in generation of the tissue compressibility for the subject body part. Yet further, at least the available patient information can be optional in determining the tissue compressibility. The tissue compressibility is comprised of values ranging from greater than 0 to less than or equal to 1.

In accordance with the present disclosure, a tension factor can be determined experimentally for each body part location and is a function of either or both of the characteristics of the subject compression garment along with a compression value indication or prescription for the person and patient information. It is a characteristic of the anatomic location on the subject body part, the compression garment for which the garment fit information is provided (e.g., brand, type, style), and the indication of compression garment use. Generated tension factor values range from greater than 0 to less than or equal to 1.

For example, and as discussed elsewhere herein, an ankle area will be expected to be "bony" and, therefore, less compressible. When a 3D image is generated of a person's ankle and the image indicates that the ankle does not comprise the typical characteristics of a bony region—that is, the ankle area is more circular in shape than expected—the imaging information can be interpreted as that body part having a characteristic of "compressibility" that is greater than 0. For a highly circular shape, and therefore one that is very different from an expected ankle shape, the compressibility factor can be closer to 1. Depending on the known characteristics of the subject compression garment to be fitted to that patient (e.g., manufacturer characteristics, type of weave, etc.) and compression values indicated for the person (e.g., mm Hg at the ankle, etc.), the subject body part characteristics—here an ankle—derived from the images can be incorporated to generate a tension factor of between 0 to 1.

With respect to the garment characteristics, each brand of compression garment will have features associated with the compression provided by the manufacturer. Moreover, and as further discussed herein, different weave techniques (e.g., flat knit or circular knit) garments will have features associated therewith. Such manufacturer-related and weave-related techniques are known or can readily be determined by one of ordinary skill in the art without undue experimentation. The compression value to be applied to the subject body part can be a therapeutic amount of compression to be applied to the subject body part as determined by a clinician or otherwise.

In addition, the tension circumference can be further modified using a geometric information modifier, a patient information modifier, or both. The geometric information modifier, which can be optional, comprises an experimentally-determined spectrum that acts as a modifier of the tension factor based upon the derived geometric characteristics of the individual. The values can range from greater than or equal to 0 to less than 1. It is unique to each person, and it is a function of various geometric measurements, which in a subject body part can include, but is not limited to:
- Diameter;
- Circumference;
- Curvature;
- Circularity;
- Cross-sectional shape;
- Axial contour pattern;
- Regional shape derivatives; and/or
- Regional geometric ratios.

A combination of the geometric measures can be evaluated based upon defined thresholds to determine corresponding scores of 1 (satisfies a comparison criterion for the defined threshold) or 0 (does not satisfy the comparison criterion for the defined threshold), which can be summed and normalized to determine the geometric information modifier as will be illustrated below. The geometric measurements can be determined from processing of the acquired 3D images taken of the subject body part, and used to determine one or more geometric information modifier for locations in the subject body part.

The patient information is an experimentally-determined spectrum that can operate as a patient information modifier of the tension factor based upon the personal information of the individual. In short, when used to generate tension values, the patient information can serve to validate or confirm the results obtained solely from imaging information. The values generated for a range from greater than or equal to 0 to less than 1. The generated value is unique to each individual, and can be a function of demographic and/or personal health information available for an individual patient or a group of patients, which could include but is not limited to:
- Age;
- Weight;
- Sex;
- BMI (body mass index);
- Lymphedema diagnosis;
- Activity level; and/or
- Medical history or diagnosed conditions.

A combination of the demographic and/or personal health factors can be evaluated based upon defined thresholds to determine corresponding scores of 1 (satisfies a comparison criterion for the defined threshold) or 0 (does not satisfy the comparison criterion for the defined threshold), which can be summed and normalized to determine the patient information modifier as will be illustrated below. Patient information can be obtained from a medical or health record, obtained via input to a set of queries, or a combination thereof. One or more generated patient information values can also be determined by a clinician or the patient herself, and can take into account the acquired 3D images of the subject body part. For example, the images may be considered by the clinician in the context of the medical or health record when determining the patient information modifier. The generated values can be used to determine one or more patient information modifier for locations in the subject body part. The patient information modifier can be solely unique to an individual patient, can be relevant to a group/demographic of patients, or a combination thereof.

The tension circumference (tC) is defined as the outer circumference (oC) multiplied by the tissue compressibility (TC). It can be written as:

$$tC = oC * TC.$$

The tissue compressibility (TC) is defined as the tension factor (TF) multiplied by 1 minus the geometric information modifier (1−G) and/or 1 minus the patient information modifier (1−P). If both the geometric information modifier and the patient information modifier are used, it can be written as:

$$TC = TF*(1-G)*(1-P).$$

In equation form, the tissue compressibility can be substituted by its components such that the tension circumference can be written as:

$$tC = oC * TF * (1-G) * (1-P).$$

The tension circumferences can then be calculated independently in each location necessitated by the compression garment manufacturing such that:

$$tC_1 = oC_1 * TF_1 * (1-G_1) * (1-P_1)$$

$$tC_2 = oC_2 * TF_2 * (1-G_2) * (1-P_2)$$

$$tC_3 = oC_3 * TF_3 * (1-G_3) * (1-P_3)$$

. . .

$$tC_n = oC_n * TF_n * (1-G_n) * (1-P_n).$$

Alternatively or, optionally, in 725 compression garments can be generated that are specifically configured for the body part or body area, to be worn on the body part or body part area at 730. A monitoring step 735 can incorporate additional image acquisition 710, etc., for the previously selected and imaged body part or body area. If the generated compression garment is worn in 730, monitoring step 735 can occur to assess whether wearing such compression garment in step 730 results in an improvement or a change in the shape of the body part.

To understand the process, consider the following illustrative example. A 65 year old male patient is being fit for a custom knee-high compression garment from Brand X and Model Y for the treatment of lymphedema. To properly fit the garment, various outer circumferences, tension circumferences, and lengths will be determined for proper fitting of the compression garment.

A key landmark that can be used for proper fit of a custom knee-high compression garment is typically the person's ankle, at least because this can comprise the distal location from which a compression garment compression value is applied to the patient body part. The location of the ankle could be determined by finding the smallest outer circumference identified above the malleolus, and the corresponding length could be measured from this location to the floor.

In this illustration, a tension factor can be determined experimentally for this anatomic location of the ankle, along with information associated with the brand and model of garment based on the relative circularity (or lack thereof) in the subject body part location. For example, the tension factor assigned to this characteristic can be assigned as 0.85 based upon the acquired 3D images of the body part.

A geometric information modifier can also be determined experimentally to be influenced by ankle cross-section circularity, medial and lateral contour derivatives, foot/ankle circumference derivative, and proximal/distal circumference derivatives. For instance, each relevant factor in the geometric information modifier could be determined to be scored as a 0 or a 1 depending upon whether the corresponding measurement exceeds a defined threshold. The factor scores can be summed and normalized by the possible total to determine the geometric information modifier. For example, the generated geometric information modifier can be assigned as 0.1 based on information for the body part of the patient.

A personal information modifier can also be determined experimentally as influenced by age, sex, and lymphedema diagnosis. Each relevant factor in the personal information modifier could be determined to be scored as a 0 or a 1 depending upon whether the corresponding measurement exceeds a defined threshold. The factor scores can be summed and normalized by the possible total to determine the personal information modifier. For example, the personal information modifier can be assigned as 0.05.

The determined information may then be used to determine the tissue compressibility information including the tension circumference. In this illustrative example, if the outer circumference determined at the ankle was 20 centimeters, then using all of the determined modifiers the tension circumference would be calculated as 20 cm*0.85*(1−0.1)*(1−0.05)=14.5 cm. Other combinations of the geometric and patient information modifiers can be used with the tension factor as can be understood. This process can be repeated for every measurement relevant for manufacturing of the compression garment for inclusion in compression garment fit information or, alternatively, compression garment selection information.

Figure 8:
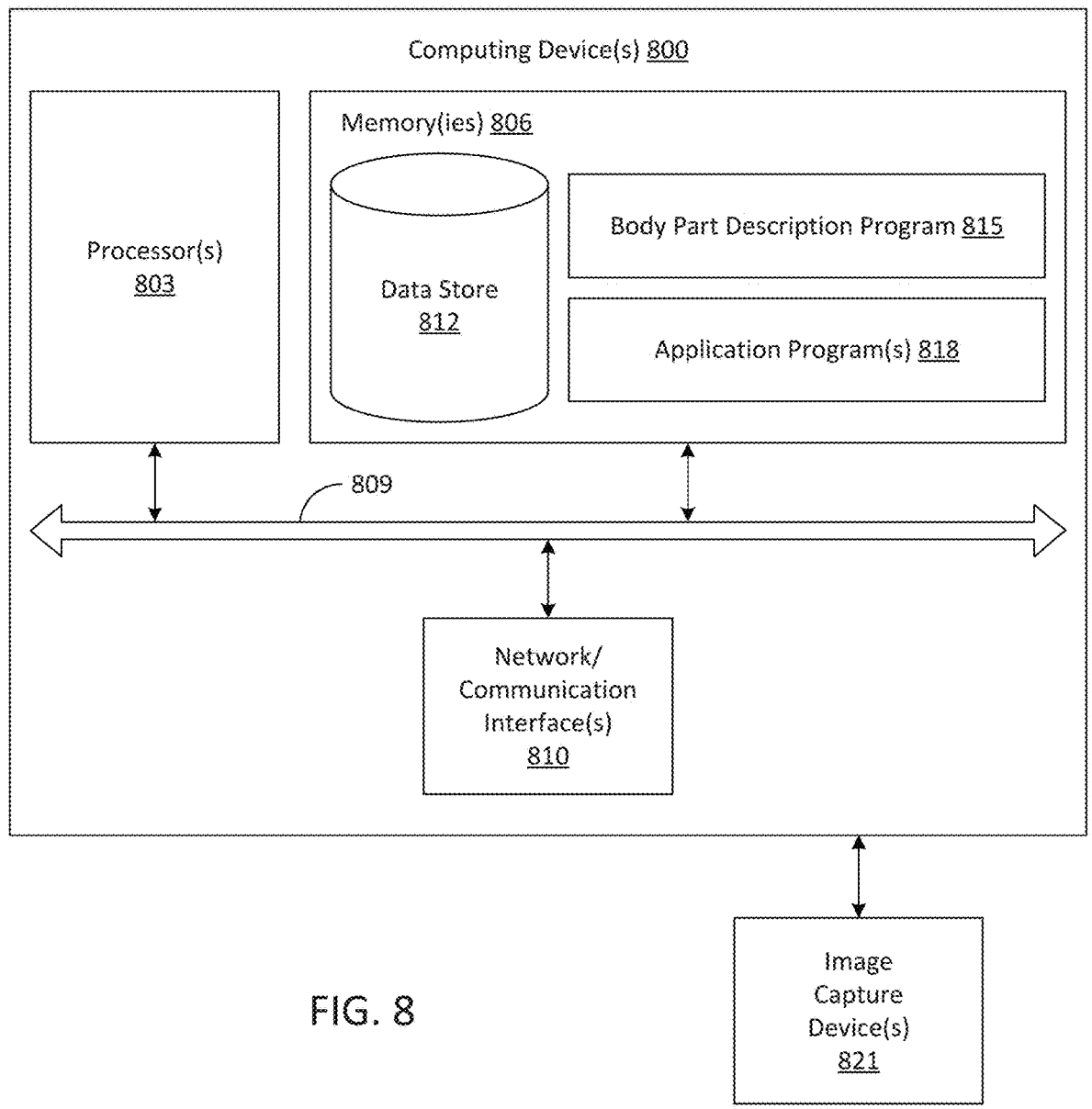
FIG. 8 is a schematic diagram illustrating an example of a computing system that can be used to derive body part description information for fitting compression garments, in accordance with various embodiments of the present disclosure.

With reference to FIG. 8, shown is a schematic block diagram of a computing device 800. In some embodiments, among others, the computing device 800 may represent a mobile device (e.g., a smartphone, tablet, computer, etc.). Each computing device 800 includes at least one processor circuit, for example, having a processor 803 and a memory 806, both of which are coupled to a local interface 809. To this end, each computing device 800 may comprise, for example, at least one server computer or like device, which can be utilized in a cloud based environment. The local interface 809 may comprise, for example, a data bus with an accompanying address/control bus or other bus structure as can be appreciated.

In some embodiments, the computing device 800 can include one or more network/communication interfaces 810. The network/communication interfaces 810 may comprise, for example, a wireless transmitter, a wireless transceiver, and/or a wireless receiver. As discussed above, the network interface 810 can communicate to a remote computing device using a Bluetooth, WiFi, or other appropriate wireless protocol. As one skilled in the art can appreciate, other wireless protocols may be used in the various embodiments of the present disclosure. In addition, the computing device 800 can be in communication with one or more image capture device(s) 821. In some implementations, an image capture device 821 can be incorporated in the computing device 800 and can interface through the locate interface 809.

Stored in the memory 806 are both data and several components that are executable by the processor 803. In particular, stored in the memory 806 and executable by the processor 803 can be a body part description program 815 and potentially other application program(s) 818. Also stored in the memory 806 may be a data store 812 and other data. In addition, an operating system may be stored in the memory 806 and executable by the processor 803.

It is understood that there may be other applications that are stored in the memory 806 and are executable by the processor 803 as can be appreciated. Where any component discussed herein is implemented in the form of software, any one of a number of programming languages may be employed such as, for example, C, C++, C #, Objective C, Java®, JavaScript®, Perl, PHP, Visual Basic®, Python®, Ruby, Flash®, or other programming languages.

A number of software components are stored in the memory 806 and are executable by the processor 803. In this respect, the term "executable" means a program file that is in a form that can ultimately be run by the processor 803. Examples of executable programs may be, for example, a compiled program that can be translated into machine code in a format that can be loaded into a random access portion of the memory 806 and run by the processor 803, source code that may be expressed in proper format such as object code that is capable of being loaded into a random access portion of the memory 806 and executed by the processor 803, or source code that may be interpreted by another executable program to generate instructions in a random access portion of the memory 806 to be executed by the processor 803, etc. An executable program may be stored in any portion or component of the memory 806 including, for example, random access memory (RAM), read-only memory (ROM), hard drive, solid-state drive, USB flash drive, memory card, optical disc such as compact disc (CD) or digital versatile disc (DVD), floppy disk, magnetic tape, holographic storage, or other memory components.

The memory 806 is defined herein as including both volatile and nonvolatile memory and data storage components. Volatile components are those that do not retain data values upon loss of power. Nonvolatile components are those that retain data upon a loss of power. Thus, the memory 806 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 803 may represent multiple processors 803 and/or multiple processor cores, and the memory 806 may represent multiple memories 806 that operate in parallel processing circuits, respectively. In such a case, the local interface 809 may be an appropriate network that facilitates communication between any two of the multiple processors 803, between any processor 803 and any of the memories 806, or between any two of the memories 806, etc. The local interface 809 may comprise additional systems designed to coordinate this communication, including, for example, performing load balancing. The processor 803 may be of electrical or of some other available construction.

Although the body part description program 815 and other application program(s) 818 described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the body part description program 815 and the application program 818, that comprises software or code can be embodied in any non-transitory computer-readable medium for use by or in connection with an instruction execution system such as, for example, a processor 803 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the body part description program 815 and the other application program(s) 818, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 800, or in multiple computing devices in the same computing environment 103. To this end, each computing device 800 may comprise, for example, at least one server computer or like device, which can be utilized in a cloud based environment. Additionally, it is understood that terms such as "application," "service," "system," "engine," "module," and so on may be interchangeable and are not intended to be limiting.

The disclosure further provides a method of identifying at least one compression value indicated for a patient for a compression garment to be worn by the patient in need of compression therapy where a defined, prescribed, or selected, compression level is applied when the garment is worn on the subject body part. The generated information can be incorporated into compression garment fit information. As would be appreciated, the compression level can be derived from by processing of 3D images generated from a first patient body part and, optionally, a second body part.

The compression garment fit information can be associated with the fabrication of a custom-fabricated compression garment configured to provide compression therapy to the patient when the garment is worn on the first patient body part by the patient. Such custom compression garments are disclosed in detail in the '581 Patent, previously incorporated herein by reference in its entirety. Yet further, such compression garment fit information can be associated with selection of a pre-fabricated compression garment configured to provide compression therapy to the patient when the garment is worn on the first patient body part by the patient. Such pre-fabricated compression garments for fitting of a leg or an arm, or portions thereof, are disclosed in detail in the '438 Patent, previously incorporated by reference.

Methods for fabricating compression garments. Compression garment manufacturing techniques commonly in use today include flat knit and circular knit. Flat knit and circular knit graduated medical compression garments are both effective for compression therapy, with the selection thereof including matters such as amount of compression needed, with flat-knit providing higher levels, comfort of the patient, and cost.

Flat-knitted garments are often used for custom garments. These are knitted on specially made machines that have a double row of needles facing each other at a 90-degree angle. A flat knit machine typically creates a sheet of fabric that must be cut and sewn by hand according to a pattern to create the finished garment. This process inherently creates seams in the garment as the edges are joined. An advantage of flat knitting is that exceedingly complex shapes can be knitted. Additionally, flat-knit garments have less stretch, and so generally provide better compression level, and therefore better compression therapies for edema/lymphedema, than circular knit garments. Flat knit garments may require custom fitting and manufacturing for optimal results in a patient in need of compression therapy. These garments come out of the machine in a flat format and then are sewn together. Flat-knitted garments are extremely well suited for larger or unusually shaped limbs and for those patients with difficult-to-manage swelling. The flat-knitting process allows for garments to bridge the gaps of any skin fold or crease can prevent the garment from digging in and irritating the skin.

Circular knit garments comprise manufacturing of a long tube of fabric to produce quite a sheer, soft, stretchy and smooth fabric. Circular-knit garments are knitted on a round cylinder. These machines have a fixed number of needles—the more needles a machine has, the wider the garment. These garments are seamless and more tubular shaped versus custom garments. Circular knitted garments typically have a bit more stretch and are best suited for patients with mild to moderate lymphedema and who have normally shaped limbs. These characteristics can make the garment more appealing; however, the fabric may often lack the ability to generate appropriate compression levels for the treatment of edema/lymphedema.

3D images can be generated for each corresponding body part for the patient, and the derived body part information can be compared to define difference (or the lack thereof) between the body parts. Comparisons can also be made between the same patient body part in a first and a second imaging event, or between corresponding body parts in a different imaging events. Compression garment fit information can be generated therefrom. Differences in the tissue compressibility of two corresponding body parts in a single patient can be determined that is each of the arms and/or each of the legs of a patient. The tissue compressibility information can be compared to derive information about differing conditions between the subject body parts within or between imaging events.

In yet another implementation, the selected patient body part is a leg, and the compression garment is in a form of a leg covering, wherein the provided at least one compression level is from 20 to 50 mm Hg, wherein the provided at least one compression level is incorporated in an area distal to a top end of the leg covering, such as location aa) or bb) in FIGS. 3A and 3B, and wherein the top end is proximal to either a calf area, knee area, a thigh area, or a gluteal area on the patient. In some implementations, the selected patient body part is an arm and the compression garment is in a form of an arm sleeve, wherein the provided at least one compression level is from 20 to 50 mm Hg, wherein the provided at least one compression level is incorporated in an area distal from a top end of the arm sleeve, and wherein the top end is proximal to a forearm area, an elbow area or an armpit area on the patient.

In testing compared against expertly trained medical compression fitters using a tape measure, the tension value derivable according to the methodology herein provides a tension value for the patient body part location that is within about 5% or less than a tension value measurement for that same patient body part location made by a trained compression garment fitter using a tape measure. The inventors have determined that that the methodology herein can provide improvements in the measurement of body parts—in particular, tissue compressibility that might be indicative of an underlying medical condition—between a first and second measurement event. Yet further, the inventors herein have determined that inter-operator variability that is typically observed in tension measurement can be markedly reduced with the methodology herein. That is, when a single patient is imaged at a first time and a second time, for example from week to week or month to month etc., different persons may be likely perform the tape measurements. Even if the persons conducting the measurements are highly trained and experienced, it is likely that each tape measurement event will be conducted with slightly different tensioning characteristics. In this regard, studies have shown that tape measurements can result in considerable variability. Moreover, it is also common that variability between measurements will occur in a single operator that conducts measurements at different time periods.

Unlike measurements obtained by people, the imaging methodology herein does not incorporate the inherent variability that is present in measurements obtained by humans. Indeed, the present methodology has been found by the inventors herein to reduce inter-measurement variability by a single trained fitter or between measuring events by up to about 75%.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

What is claimed is:

1. A method for generating compression garment fit information for a person in need of compression therapy, comprising:
   a) selecting a first body part on a person in need of compression therapy;
   b) acquiring 3D images of the first body part;
   c) processing the 3D images by a computing device, wherein the processing of the 3D images comprises deriving body part information for the first body part, the derived body part information comprising:
      i) tissue compressibility information, where:
         the tissue compressibility information is derived from each of a plurality of cross-sectional views of the first body part at a plurality of body part locations along the first body part;
      ii) outer circumference information; and
      iii) length information;
      where:
         1. the tissue compressibility information for each of the plurality of body part locations is associated with a body part tensioned circumference determined at each body part location using the derived body part information;
         2. for each of the plurality of body part locations for which a cross-sectional view is generated, each of a corresponding body part outer circumference and a corresponding body part tensioned circumference is provided; and
         3. each corresponding body part tensioned circumference is smaller than the corresponding body part outer circumference; and
   d) generating compression garment fit information from the derived body part information, where the corresponding body part tensioned circumferences and the corresponding body part outer circumference at each of the plurality of body part locations are incorporated in the compression garment fit information.

2. The method of claim 1, wherein the first body part is a leg, and the plurality of cross-sectional views comprises at least two cross-sectional views of the leg, wherein:
   a) at least one of the plurality of cross-sectional views is generated at:
      i) a location proximate to a heel bottom and a location proximate to an ankle; or
      ii) the location proximate to the ankle; and
   b) at least one of the plurality of cross-sectional views is generated at:
      i) a location proximate to ½ of a distance from the location proximate to the heel bottom and a location proximate to a popliteal region;

ii) a location proximate to ¾ of a distance from the location proximate to the ankle and the location proximate to the popliteal region;
iii) a location proximate to a bottom of a knee;
iv) the location proximate to the popliteal region;
v) a location proximate to ½ of a distance from the location proximate to the popliteal region and a location proximate to a gluteal region; or
vi) the location proximate to the gluteal region.

3. The method of claim 1, wherein the first body part is an arm, and the plurality of cross-sectional views comprises at least two cross-sectional views of the arm,
   a) wherein at least one of the plurality of cross-sectional views is generated at:
      i) a location proximate to a palm at a base of a thumb; or
      ii) a location proximate to a wrist region; and
   b) wherein at least one of the plurality of cross-sectional views is generated at:
      i) a location proximate to ½ of a distance from the location proximate to the wrist region and a location proximate to an elbow region;
      ii) the location proximate to the elbow region;
      iii) a location proximate to ½ of a distance from the location proximate to the elbow region and a location proximate to an armpit region; or
      iv) the location proximate to the armpit region.

4. The method of claim 1, wherein the tissue compressibility information is generated by:
   a) providing outer circumferences for at least two adjacent body part locations; and
   b) providing adjacent body part outer circumference ratios for each of the at least two adjacent body part locations.

5. The method of claim 4, wherein the first body part is a leg and the at least two adjacent body part locations comprise a first adjacent body part location and a second adjacent body part location, where:
   i) the first adjacent body part location comprises a location proximate to a heel bottom and the second adjacent body part location comprises a location proximate to an ankle;
   ii) the first adjacent body part location comprises a location proximate to the ankle and the second adjacent body part location comprises a location proximate to ½ of a distance from the location proximate to the ankle and a popliteal area;
   iii) the first adjacent body part location comprises a location proximate to ½ of a distance from the location proximate to the ankle and the second adjacent body part location comprises a location proximate to ¾ of a distance to a location proximate to a lower knee area;
   iv) the first adjacent body part location comprises a location proximate to the lower knee area and the second adjacent body part location comprises a location proximate to the popliteal area;
   v) the first adjacent body part location comprises a location proximate to the popliteal area and the second adjacent body part location comprises a location proximate to ½ of a distance from a location proximate to the popliteal area and a gluteal area; or
   vi) the first adjacent body part location comprises a location proximate to ½ of a distance from the location proximate to the popliteal area and the second adjacent body part location comprises a location proximate to the gluteal area.

6. The method of claim 4, wherein the body part is an arm and the at least two adjacent body part locations comprise a first adjacent body part location and a second adjacent body part location, where:
   i) the first adjacent body part location comprises a location proximate to a palm at a base of a thumb and the second adjacent body part location comprises a location proximate to a wrist area;
   ii) the first adjacent body part location comprises the location proximate to the wrist area and the second adjacent body part location comprises a location proximate to ½ of a distance from the location proximate to the wrist area and a location proximate to an elbow area;
   iii) the first adjacent body part location comprises the location proximate to ½ of the distance between the wrist area and the elbow area and the second adjacent body part location comprises a location proximate to the elbow area;
   iv) the first adjacent body part location comprises the location proximate to the elbow area and the second adjacent body part location comprises a location proximate to ½ of a distance from the location proximate to the elbow area and a location proximate to an armpit area; or
   v) the first adjacent body part location comprises the location proximate to the elbow area and the second adjacent body part location comprises a location proximate to the armpit area.

7. The method of claim 1, wherein the compression garment fit information is used to fabricate a custom-fabricated compression garment configured to provide compression therapy to the person when the garment is worn on the first body part.

8. The method of claim 1, wherein the compression garment fit information is used in the selection of a pre-fabricated compression garment configured to provide compression therapy to the person when the garment is worn on the first body part.

9. The method of claim 1, wherein:
   a. the first body part is an arm;
   b. a compression garment fabricated from the compression garment fit information is in a form of an arm sleeve and incorporates a compression value of from 20 to 50 mm Hg; and
   c. the compression garment is configured to apply the compression value to the body part when the compression garment is worn by the person.

10. The method of claim 1, wherein:
   a) the first body part is a leg;
   b) a compression garment fabricated from the compression garment fit information is in a form of a leg sleeve and incorporates a compression value of from 20 to 50 mm Hg; and
   c) the compression garment is configured to apply the compression value to the body part when the compression garment is worn by the person.

11. A method for generating compression garment fit information for a person in need of compression therapy, comprising:
   a) selecting first and second corresponding body parts in the person, where each of the first and second corresponding body parts is all or part of first and second arms or all or part of first and second legs;
   b) acquiring 3D images of the first and second corresponding body parts at a plurality of corresponding locations for each of the first and second body parts;

c) processing the 3D images by a computing device, wherein the processing of the 3D images comprises deriving for each of the first and second corresponding body parts information comprising:
  i) tissue compressibility information;
  ii) outer circumference information; and
  iii) length information;
d) comparing the tissue compressibility information for each of the first and second corresponding body parts at a plurality of corresponding body part locations, thereby generating information about a difference in tissue compressibility between each of a plurality of corresponding body part locations for each of the first and second corresponding body parts; and
e) generating compression garment fit information for either or both of the first and second corresponding body parts from the body part outer circumference information, tissue compressibility difference information, and length information.

12. The method of claim 11, wherein:
a) the tissue compressibility information is derived from the processing of the 3D images at a plurality of cross-sectional views for each of the plurality of corresponding body part locations along each of the first and second corresponding body parts and is associated with body part tensioned circumferences at each of the plurality of corresponding body part location;
b) for each body part location of the plurality of corresponding body part locations along each of the first and second corresponding body parts for which cross-sectional view is generated, a corresponding body part outer circumference and a body part tensioned circumference is generated;
c) each body part tensioned circumference for each body part location is smaller than the corresponding body part outer circumference; and
d) each of the body part tensioned circumferences and each of the corresponding body part outer circumferences are incorporated in the compression garment fit information.

13. The method of claim 11, wherein:
a) each of the first and second corresponding body parts comprise the first and second legs and each of the plurality of cross-sectional views comprises at least two cross-sectional views of each of the first and second legs;
b) at least one of the plurality of cross-sectional views for each of the first and second legs is generated at:
  i) a location proximate to a heel bottom and a location proximate to an ankle; or
  ii) the location proximate to the ankle; and
c) at least one of the plurality of cross-sectional views of the first and second legs is generated at:
  i) a location proximate to ½ of a distance from the location proximate to the heel bottom and a location proximate to a popliteal region;
  ii) a location proximate to ¾ of a distance from the location proximate to the ankle and the location proximate to the popliteal region;
  iii) a location proximate to a bottom of a knee;
  iv) the location proximate to the popliteal region;
  v) a location proximate to ½ of a distance from the location proximate to the popliteal region and a location proximate to a gluteal region; or
  vi) the location proximate to the gluteal region.

14. The method of claim 11, wherein:
a) each of the first and second corresponding body parts comprise the first and second arms, and each of the plurality of cross-sectional views comprises at least two cross-sectional views of each of the first and second arms;
b) at least one of the plurality of cross-sectional views is generated at
  i) a location proximate to a palm at a base of a thumb; or
  ii) a location proximate to a wrist region; and
wherein at least one of the plurality of cross-sectional views is generated at:
  iii) a location proximate to ½ of a distance from the location proximate to the wrist region and a location proximate to an elbow region;
  iv) the location proximate to the elbow region;
  v) a location proximate to ½ of a distance from the location proximate to the elbow region and an area proximate to an armpit region; or
  vi) the area proximate to the armpit region.

15. The method of claim 11, wherein the compression garment fit information includes a compression value configured to provide compression therapy to the person when the person is wearing a compression garment incorporating a tension value on either of the first or second corresponding body parts.

16. The method of claim 11, wherein the compression garment fit information is used to fabricate a custom-fabricated compression garment configured to provide compression therapy to the person when the garment is worn by the person.

17. The method of claim 11, wherein the compression garment fit information is used in the selection of a pre-fabricated compression garment configured to provide compression therapy to the person when the garment is worn by the person.

18. The method of claim 11, wherein the first and second corresponding body parts are the first and second legs and the tissue compressibility difference information is generated by:
a) comparing outer circumference information for at least two adjacent body part locations each including adjacent body part locations for the first and second legs, wherein the at least two adjacent body part locations comprise a first adjacent body part location and a second adjacent body part location, where:
  i) the first adjacent body part location comprises a location proximate to a heel bottom and a location proximate to an ankle;
  ii) the first adjacent body part location comprises a location proximate to the ankle and the adjacent body part location comprises a location proximate to ½ of a distance from the location proximate to the ankle and a popliteal area;
  iii) the first adjacent body part location comprises a location proximate to ½ of a distance from the location proximate to the ankle and the popliteal area and the second adjacent body part location comprises a location proximate to ¾ of a distance to a location proximate to the lower knee area;
  iv) the first adjacent body part location comprises a location proximate to the lower knee area and the second adjacent body part location comprises a location proximate to the popliteal area;
  v) the first adjacent body part location comprises a location proximate to the popliteal area and the second adjacent body part location comprises a location proximate to ½ of a distance from a location proximate to a gluteal area; or vi) the first adjacent body part location pair comprises a location proximate to ½ of a distance from the location proximate to the popliteal area and the second adjacent body part location comprises a location proximate to the gluteal area; and b) deriving an adjacent body part outer circumference ratio for each of the at least two adjacent body part locations.

19. The method of claim 11, wherein the first and second corresponding body parts are the first and second arms and the tissue compressibility difference information is generated by:

a) comparing outer circumferences information for at least two adjacent body part locations each including adjacent body part locations for the first and the second arms, wherein the at least two adjacent body part location comprise a first adjacent body part location and a second adjacent body part location, where:

i) the first adjacent body part location comprises a location proximate to a palm at a base of a thumb and the second adjacent body part location comprises a location proximate to a wrist area;

ii) the first adjacent body part location comprises a location proximate to the wrist area and the second adjacent body part location comprises a location proximate to ½ of a distance from the location proximate to the wrist area and a location proximate to an elbow area;

iii) the first adjacent body part location comprises a location proximate to ½ of the distance from the location proximate to the wrist area and the second adjacent body part location comprises the location proximate to the elbow area and a location proximate to the elbow area;

iv) the first adjacent body part location comprises a location proximate to the elbow area and the second adjacent body part location comprises a location proximate to ½ of a distance between the location proximate to the elbow area and a location proximate to an armpit region; or v) the first adjacent body part location comprises a location proximate to the elbow area and the second adjacent body part location comprises a location proximate to the armpit region; and b) deriving an adjacent body part outer circumference ratio for each of the at least two adjacent body part locations.

* * * * *